US009651481B2

(12) United States Patent
DeGreeve et al.

(10) Patent No.: US 9,651,481 B2
(45) Date of Patent: *May 16, 2017

(54) METHOD AND APPARATUS FOR LIBERATING GASES FROM DRILLING FLUID

(71) Applicant: PASON SYSTEMS CORP., Calgary (CA)

(72) Inventors: Jason Alexander DeGreeve, Calgary (CA); Sean William Lyons Unrau, Calgary (CA); Marceau Ernest van Beurden, Calgary (CA); Ryan Henricus van Beurden, Calgary (CA)

(73) Assignee: PASON SYSTEMS CORPORATION, Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,881

(22) Filed: Jan. 17, 2014

(65) Prior Publication Data

US 2014/0130671 A1    May 15, 2014

Related U.S. Application Data

(63) Continuation of application No. 12/917,095, filed on Nov. 1, 2010, now Pat. No. 8,632,625.
(Continued)

(51) Int. Cl.
*E21B 21/06* (2006.01)
*G01N 21/3504* (2014.01)
(Continued)

(52) U.S. Cl.
CPC ..... *G01N 21/3504* (2013.01); *B01D 19/0042* (2013.01); *B01D 19/0052* (2013.01);
(Continued)

(58) Field of Classification Search
CPC .......... E21B 21/067; G01N 2001/2267; G01N 33/2823; G01N 1/2247
See application file for complete search history.

(56) References Cited

U.S. PATENT DOCUMENTS

| 1,993,984 | A | * | 3/1935 | Wulle | ...................... H02G 3/06 174/13 |
| 2,071,393 | A | * | 2/1937 | Doherty | ........................ 96/196 |

(Continued)

FOREIGN PATENT DOCUMENTS

| CA | 2236615 A1 | 10/1999 |
| CA | 2256248 A1 | 6/2000 |

(Continued)

OTHER PUBLICATIONS

"SKA DDR Torque Motos", Motor Power Company, 2007.*
(Continued)

*Primary Examiner* — David A Rogers
(74) *Attorney, Agent, or Firm* — Katten Muchin Rosenman LLP

(57) ABSTRACT

A gas trap includes a sample enclosure, a bubbler enclosure, an agitator, and a brushless, DC motor. The sample enclosure has a liquid inlet, a gas sample outlet, and a sample enclosure wall with a sample enclosure wall portion and a shared wall portion. The bubbler enclosure has a bubbler air inlet, a bubbler air outlet, and a bubbler enclosure wall with a bubbler enclosure wall portion and the shared wall portion. The sample and bubbler enclosures are fluidly coupled through the shared wall portion so that sufficiently pressurized bubbler air entering through the bubbler air inlet maintains the drilling fluid in the sample enclosure at a level determined by the location of the bubbler air outlet when the liquid inlet and the bubbler air outlet are both submerged in the drilling fluid.

21 Claims, 16 Drawing Sheets

Related U.S. Application Data

(60) Provisional application No. 61/355,951, filed on Jun. 17, 2010.

(51) Int. Cl.
    G01N 21/35    (2014.01)
    B01D 19/00    (2006.01)
    E21B 49/00    (2006.01)
    G01V 8/02     (2006.01)

(52) U.S. Cl.
    CPC ............ E21B 21/067 (2013.01); E21B 49/00
    (2013.01); E21B 49/005 (2013.01); G01N
    21/35 (2013.01); G01V 8/02 (2013.01)

(56) References Cited

U.S. PATENT DOCUMENTS

| | | | | |
|---|---|---|---|---|
| 2,096,174 A * | 10/1937 | Hamill | | 96/214 |
| 2,514,690 A * | 7/1950 | Bliss et al. | | 73/19.09 |
| 2,704,658 A * | 3/1955 | Gordon | | 366/329.1 |
| 2,792,072 A * | 5/1957 | Moore | | 96/214 |
| 3,118,738 A * | 1/1964 | Jamieson | | 422/83 |
| 3,617,614 A * | 11/1971 | Henry | | H02G 3/0616 174/652 |
| 3,775,551 A * | 11/1973 | Prehmus | | H01H 9/042 174/542 |
| 3,922,904 A * | 12/1975 | Williams et al. | | 73/19.1 |
| 3,973,930 A * | 8/1976 | Burgess | | 95/261 |
| 4,084,946 A * | 4/1978 | Burgess | | 96/188 |
| 4,214,879 A * | 7/1980 | Whetstone et al. | | 96/196 |
| RE30,836 E * | 12/1981 | Bunnelle | | 96/214 |
| 4,326,863 A * | 4/1982 | Day et al. | | 96/182 |
| 4,358,298 A * | 11/1982 | Ratcliff | | 96/189 |
| 4,394,140 A * | 7/1983 | Liljestrand | | 96/188 |
| 4,492,862 A | 1/1985 | Grynberg et al. | | |
| 4,535,275 A * | 8/1985 | Muller | | 318/400.25 |
| 4,549,037 A * | 10/1985 | Bawa | | H02G 3/088 174/667 |
| 4,628,392 A * | 12/1986 | Didier | | E21B 33/0407 200/51.04 |
| 4,635,735 A | 1/1987 | Crownover | | |
| 4,676,574 A * | 6/1987 | Grosso | | H01R 13/527 439/271 |
| 5,090,256 A * | 2/1992 | Issenmann | | 73/863.23 |
| 5,199,509 A * | 4/1993 | Wright et al. | | 175/50 |
| 5,648,603 A * | 7/1997 | Hanson | | 73/152.02 |
| 5,712,481 A | 1/1998 | Welch et al. | | |
| 5,959,377 A * | 9/1999 | Horng | | H02K 29/06 310/180 |
| 6,389,878 B1 * | 5/2002 | Zamfes | | 73/19.09 |
| 6,392,322 B1 * | 5/2002 | Mares | | B23Q 5/58 310/12.04 |
| 6,546,818 B2 | 4/2003 | Taylor et al. | | |
| 6,572,422 B2 * | 6/2003 | Kirkwood et al. | | 440/67 |
| 6,666,099 B2 * | 12/2003 | Taylor | | 73/863.12 |
| 6,726,190 B2 | 4/2004 | Malpass et al. | | |
| 6,850,019 B2 * | 2/2005 | Gerfast | | H02P 6/085 310/156.01 |
| 7,032,444 B2 * | 4/2006 | Breviere et al. | | 73/152.23 |
| 7,132,657 B2 | 11/2006 | Smith | | |
| 7,389,704 B2 * | 6/2008 | Desrochers et al. | | 73/863.33 |
| 7,395,691 B2 | 7/2008 | Sterner et al. | | |
| 7,421,881 B2 * | 9/2008 | Nathan | | B01D 19/0005 73/19.09 |
| 7,465,426 B2 * | 12/2008 | Kerherve et al. | | 422/68.1 |
| 7,486,041 B2 * | 2/2009 | Wasson | | G04C 3/143 318/432 |
| 7,569,969 B2 * | 8/2009 | Nakano | | H02K 1/24 310/264 |
| 7,779,667 B2 * | 8/2010 | Evrard | | 73/19.09 |
| 7,794,252 B2 * | 9/2010 | Sauer | | H01R 13/622 439/181 |
| 7,794,527 B2 * | 9/2010 | Sterner | | 96/157 |
| 8,030,809 B2 * | 10/2011 | Horng | | H02K 1/146 310/43 |
| 2003/0230716 A1 | 12/2003 | Russell | | |
| 2004/0265176 A1 * | 12/2004 | Kerherve et al. | | 422/68.1 |
| 2006/0093523 A1 | 5/2006 | Norman | | |
| 2006/0202122 A1 | 9/2006 | Gunn et al. | | |
| 2006/0254421 A1 * | 11/2006 | Boone | | 95/260 |
| 2006/0261192 A1 * | 11/2006 | Haas | | B25J 19/0079 239/533.1 |
| 2006/0261684 A1 * | 11/2006 | Sonohara | | H02K 5/225 310/49.08 |
| 2007/0159017 A1 * | 7/2007 | Martin | | H02K 5/136 310/88 |
| 2007/0159018 A1 * | 7/2007 | Martin | | H02K 5/136 310/88 |
| 2008/0245960 A1 | 10/2008 | Csutak | | |
| 2009/0008560 A1 | 1/2009 | Gunn et al. | | |
| 2009/0049889 A1 | 2/2009 | Pop et al. | | |
| 2010/0027004 A1 | 2/2010 | Bonyuet et al. | | |
| 2010/0108020 A1 * | 5/2010 | Miretti | | H02G 3/0675 123/198 D |
| 2010/0282959 A1 | 11/2010 | Dong et al. | | |
| 2011/0018337 A1 * | 1/2011 | King et al. | | 303/13 |
| 2013/0056626 A1 | 3/2013 | Shen | | |

FOREIGN PATENT DOCUMENTS

| | | | |
|---|---|---|---|
| CA | 2425423 A1 | 4/2002 | |
| CA | 2461933 A1 | 9/2004 | |
| CA | 2524288 A1 | 11/2004 | |
| CA | 2605830 A1 | 11/2006 | |
| CA | 2653580 A1 | 2/2008 | |
| CA | 2645837 A1 | 4/2008 | |
| CA | 2669434 A1 | 5/2008 | |
| CA | 2618462 A1 | 7/2008 | |
| CA | 2660805 A1 | 4/2009 | |
| JP | 09149567 A | * | 6/1997 |
| WO | 2006/097670 A1 | 9/2006 | |
| WO | 2008/095053 A1 | 8/2008 | |
| WO | 2008/119679 A1 | 10/2008 | |
| WO | 2008/124286 A1 | 10/2008 | |
| WO | 2008/135416 A1 | 11/2008 | |
| WO | 2009/085496 A1 | 7/2009 | |

OTHER PUBLICATIONS

"Kollmorgen Goldline Brushless Motor Series", Kollmorgen, 2004.*

The Pason Total Gas (TGAS) System, Jun. 29, 2012, retrieved using the Internet Archive Wayback Machine on Jun. 19, 2013.

Bloodhound Gas Detector (chromatograph and IR detector combined) from iBall Instruments Mud Logging System, Feb. 9, 2010, retrieved using the Internet Archive Wayback Machine on Jun. 19, 2013.

Bloodhound Gas Detector (chromatograph and IR detector combined) from iBall Instruments Mud Logging System, Apr. 21, 2010, retrieved using the Internet Archive Wayback Machine on Jun. 19, 2013.

Bloodhound Gas Detector (chromatograph and IR detector combined) from iBall Instruments Mud Logging System, current web page as of Jun. 19, 2013, <www.iballinstruments.com>.

MD Totco Wellsite Gas Watch (dual IR detectors), May 5, 2010, retrieved using the Internet Archive Wayback Machine on Jun. 19, 2013.

MD Totco Wellsite Gas Watch (dual IR detectors), current web page as of Jun. 19,2013, <http://www.nov.com/>.

RigSat Gas Detector (single IR detector), Oct. 25, 2008, retrieved using the Internet Archive Wayback Machine on Jun. 19, 2013.

RigSat Gas Detector (single IR detector), current web page as of Jun. 19, 2013, <http://www.rigsat.com/rig-gas-detector/>.

Total Gas Systems (single IR detector), retrieved using the Internet Archive Wayback Machine on Jun. 19, 2013.

Total Gas Systems (single IR detector), current web page as of Jun. 19, 2013, <http://www.totalgas.ca/hardware.html>.

(56) References Cited

OTHER PUBLICATIONS

Continental Chromatograph (chromatograph plus manned service), retrieved using the Internet Archive Wayback Machine on Jun. 19, 2013.
Continental Chromatograph (chromatograph plus manned service), current web page as of Jun. 19, 2013, <html://www.continental-labs.ab.ca/gas_chrom.htm>.
Continental Gas Detector (single filament-based detector), May 29, 2013, retrieved using the Internet Archive Wayback Machine on Jun. 19, 2013.
Continental Gas Detector (single filament-based detector), current web page as of Jun. 19, 2013, <html://www.continental-labs.ab.ca/mp2500.htm>.
Weatherford GC-Tracer Surface Gas Detector, Feb. 17, 2009, retrieved from, <http://www.weatherford.com/weatherford/groups/web/documents/weatherfordcorp/WFT100978.pdf>.
Weatherford GC-Tracer Surface Gas Detector, current web page as of Jun. 19, 2013, <http://www.weatherford.com>.
MSI MLogger Series Gas Detector, Feb. 12, 2010, retrieved using the Internet Archive Wayback Machine on Jun. 19, 2013.
MSI MLogger Series Gas Detector, current web page as of Jun. 19, 2013, <http://www.mudlogsys.com/index.html>.
Infratec 4 Discrete Channel IR Detector (NDIR technology), Oct. 30, 2008, retrieved from <http://www.infratec-Infrared.com/Data/LIM-214.pdf>.
Infratec Fabry-Perot Tunable Detector (uses a micro-machined Fabry-Perot tunable filter and detector in a single device), Oct. 30, 2008, retrieved from <http://www.infratec-infrared.com/Data/LFP-3041L.pdf>.
Fourier Transform Spectroscopy (FTIR technology), Feb. 8, 2010, retrieved from Wikipedia using the Internet Archive Wayback Machine on Jun. 19, 2013.
Fourier Transform Spectroscopy (FTIR technology), entry from Wikipedia on of Jun. 19, 2013, <http://en.wikipedia.org/wiki/Main_Page>.
Tunable Diode Laser Absorption Spectroscopy, Dec. 8, 2008, retrieved from Wikipedia using the Internet Archive Wayback Machine on Jun. 19, 2013.
Tunable Diode Laser Absorption Spectroscopy, retrieved from Wikipedia on Jun. 19, 2013, <http://en.wikipedia.org/wiki/Main_Page>.
Gas chromatography, retrieved from Wikipedia, retrieved on Jun. 19, 2013, <http://en.wikipedia.org/wiki/Main_Page>.
Thermal Conductivity Detector, Oct. 6, 2009, retrieved from Wikipedia using the Internet Archive Wayback Machine on Jun. 19, 2013.
Thermal Conductivity Detector, retrieved from Wikipedia on Jun. 19, 2013, <http://en.wikipedia.org/wiki/Main_Page>.
Diversified Well Logging Inc.'s QGM Gas Trap, Apr. 23, 2009, retrieved from <http://www.dwl-usa.net/images/DWL_QGM.pdf> on Jun. 19, 2013.
Iball Cavitation-Style Trap, Dec. 12, 2009, retrieved using the Internet Archive Wayback Machine on Jun. 19, 2013.
Iball Cavitation-Style Trap, Jul. 18, 2011, retrieved using the Internet Archive Wayback Machine on Jun. 19, 2013.
Iball Cavitation-Style Trap, current web page as of Jun. 19, 2013, <www.iballinstruments.com>.
Schlumberger pamphlet, "CFA Composition Fluid Analyzer", dated Mar. 2004.
Kollmorgen: Mounting, Design, and Installation of Frameless Motors, Nov. 19, 2003, from <www.DanaherMotion.com>.

\* cited by examiner

METHOD AND APPARATUS FOR LIBERATING GASES FROM DRILLING FLUID

CROSS REFERENCE TO RELATED APPLICATION

This application is a continuation of U.S. patent application Ser. No. 12/917,095, filed Nov. 1, 2010, which claims the benefit of U.S. Provisional Patent Application No. 61/355,951, filed Jun. 17, 2010, the entire contents of each of which are hereby incorporated by reference.

TECHNICAL FIELD

The present disclosure is directed at a method and apparatus for speciating hydrocarbons and at a method and apparatus for liberating gases from drilling fluid. More particularly, the present disclosure is directed at a gas analyzer for speciating any one or more of methane, ethane, propane, butane and pentane conveyed in a drilling fluid, and at a gas trap that can be used with the gas analyzer.

BACKGROUND

During oil and gas well drilling, drilling fluid (also known as "drilling mud") is typically pumped from the surface down the well that is being drilled. This may be done for multiple reasons. The drilling fluid may, for example, provide cooling, lubrication, and may act as a medium through which communication signals that originate downhole propagate to the surface. When drilling fluid is used in oil and gas drilling, hydrocarbons from the formation that is being drilled come into contact with the drilling fluid and are absorbed by the drilling fluid. The drilling fluid transports these absorbed hydrocarbons to the surface where they can be separated from the drilling fluid and analyzed. The hydrocarbons present in the drilling fluid can indicate the likelihood that the well being drilled will produce significant quantities of oil or gas.

BRIEF DESCRIPTION OF THE DRAWINGS

In the accompanying drawings, which illustrate one or more exemplary embodiments.

DETAILED DESCRIPTION

Figure 1:
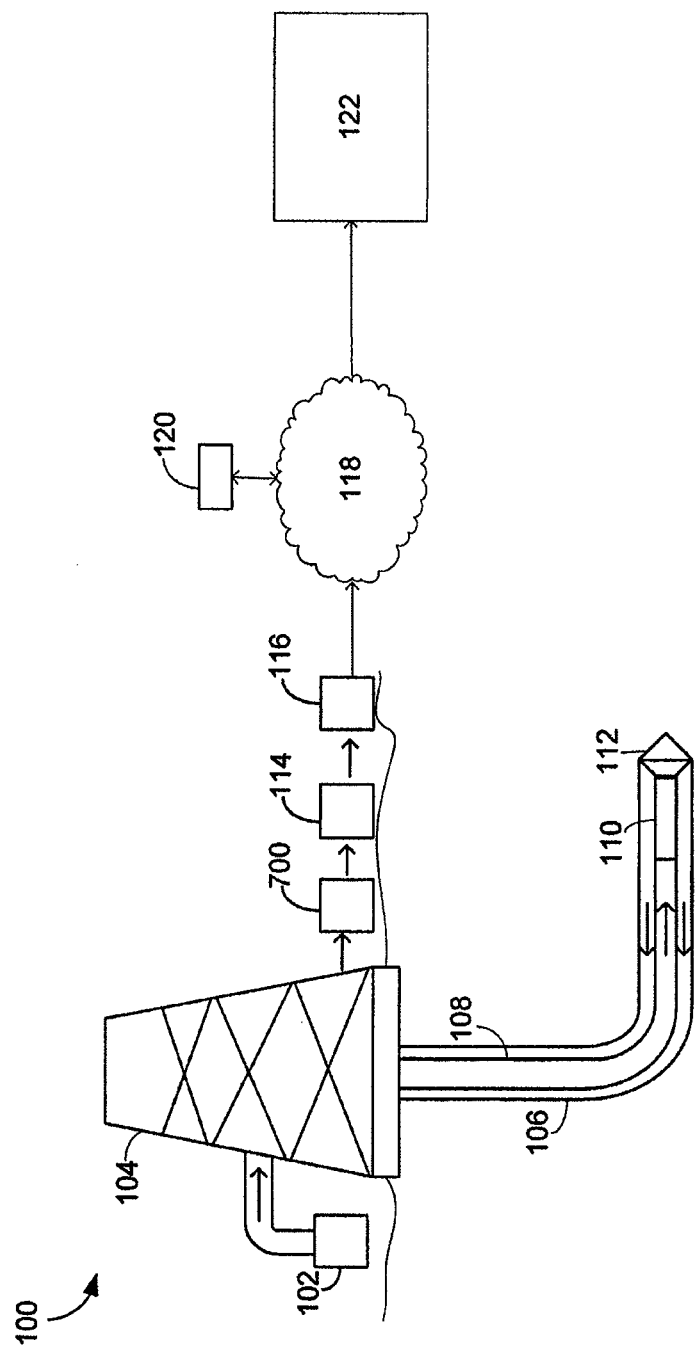
FIG. 1 is a block diagram of a drilling site that has on it a gas analyzer according to a first embodiment.

According to a first aspect, there is provided a method for analyzing a gas sample conveyed in a drilling fluid. The method includes liberating the gas sample from the drilling fluid, wherein the gas sample comprises one or more of methane, ethane, propane, and butane; irradiating the gas sample with infrared radiation spanning a wavelength range comprising near-infrared wavelengths; simultaneously detecting absorption spectra associated with irradiating each of the one or more of methane, ethane, propane, and butane; and determining a composition of the gas sample from the absorption spectra, the composition comprising a concentration of any one or more of the methane, ethane, propane and butane.

The wavelength range can be from about 1.55 µm to about 1.85 µm.

The absorption spectra can be used to determine how much pentane is present in the gas sample, and how much carbon dioxide is present in the gas sample.

The butane may include one or both of i-butane and n-butane.

Determining the composition of the gas sample may include determining the concentrations of any two or more of the methane, ethane, propane and butane; any three or more of the methane, ethane, propane and butane; or the concentrations of each of the methane, ethane, propane and butane.

A tunable laser diode can be used to emit the infrared radiation.

Liberating the gas sample from the drilling fluid can be performed using a gas trap, and air may be pumped from an air source into the gas trap to maintain the drilling fluid at a certain height within the gas trap. The gas sample may be heated after it is liberated from the drilling fluid and the air from the air source may be heated prior to being pumped into the gas trap.

The method may also include pressurizing, in a pressure reservoir, air from the air source; and discharging pressurized air from the pressure reservoir into a flowline used to intake the gas sample from the gas trap to clear the flowline.

According to another aspect, there is provided an apparatus for analyzing a gas sample extracted from a drilling fluid. The apparatus includes a sample inlet configured to receive the gas sample, wherein the gas sample comprises one or more of methane, ethane, propane, and butane; a hydrocarbon sensor comprising a gas cell fluidly coupled to the sample inlet and configured to contain a portion of the gas sample; an infrared emitter positioned to irradiate the gas cell with infrared radiation spanning a wavelength range comprising near-infrared wavelengths; a detector aligned with a path of the infrared radiation to simultaneously detect absorption spectra associated with irradiating each of the one or more of methane, ethane, propane, and butane within the gas cell; a sample outlet fluidly coupled to the gas cell and configured to discharge the gas sample; and a processor communicatively coupled to the detector and to a memory, the memory having statements and instructions encoded thereon to configure the processor to determine a composition of the gas sample from the absorption spectra, the composition comprising a concentration of any one or more of the methane, ethane, propane and butane.

The wavelength range may be from about 1.55 µm to about 1.85 µm.

The statements and instructions encoded on the memory may further configure the processor to determine how much pentane is present in the gas sample.

The apparatus may also include a carbon dioxide detector fluidly coupled to the gas cell, and the statements and instructions encoded on the memory may further configure the processor to determine how much carbon dioxide is present in the gas sample.

The statements and instructions encoded on the memory may further configure the processor to determine how much of one or both of n-butane and i-butane are present in the gas sample.

The statements and instructions encoded on the memory may configure the processor to determine the concentrations of any two or more of the methane, ethane, propane and butane; of any three or more of the methane, ethane, propane and butane; or of each of the methane, ethane, propane and butane.

The infrared emitter may be a tunable laser diode.

The apparatus may also include a bubbler pump, a bubbler inlet and a bubbler outlet, wherein the bubbler pump is fluidly coupled to the bubbler outlet and to an air source via the bubbler inlet and is configured to pump bubbler air out through the bubbler outlet.

The apparatus may also include a gas trap configured to liberate the gas sample from the drilling fluid, and having a bubbler air port fluidly coupled to the bubbler pump via a bubbler air conduit and a gas sample port fluidly coupled to the sample inlet via a gas sample conduit, wherein the bubbler air pumped from the bubbler pump through the bubbler air conduit and into the bubbler air port maintains the drilling fluid at a certain height within the gas trap and wherein the gas sample is discharged through the gas sample port and gas sample conduit to the sample inlet.

The apparatus may also include a tubing bundle surrounding the bubbler air and gas sample conduits, the tubing bundle having a heat trace configured to heat the bubbler air and gas sample conduits.

The apparatus may also include a sample filter; and valving configurable in measurement, pressurizing and purging states. The valving can fluidly couple the sample inlet to the hydrocarbon sensor through the sample filter when in the measurement state, fluidly couple the bubbler pump to the sample filter such that pressure builds within the sample filter when in the pressurizing state, and fluidly couple the bubbler pump to the sample inlet through the sample filter when in the purging state such that pressurized air within the sample filter can be discharged through the sample inlet.

According to another aspect, there is provided an apparatus for liberating gases from drilling fluid. The apparatus includes a sample enclosure having a liquid inlet and a gas sample outlet; an agitator disposed within the sample enclosure and configured to agitate drilling fluid located within the sample enclosure to liberate gases entrained in the drilling fluid so that the gases can exit through the gas sample outlet; and a bubbler enclosure, having a bubbler air inlet and a bubbler air outlet, and fluidly coupled to the sample enclosure such that the sample and bubbler enclosures are equally pressurized so that sufficiently pressurized bubbler air entering through the bubbler air inlet maintains the drilling fluid in the sample enclosure at a level determined by the location of the bubbler air outlet when the liquid inlet and the bubbler air outlet are both submerged in the drilling fluid, and such that agitated drilling fluid enters the bubbler enclosure from the sample enclosure.

The sample enclosure may be delineated by a sample enclosure wall comprising a sample enclosure wall portion and a shared wall portion. The bubbler enclosure may be delineated by a bubbler enclosure wall comprising a bubbler enclosure wall portion and the shared wall portion. The sample enclosure and the bubbler enclosure may be fluidly coupled through the shared wall portion.

The shared wall portion can include a liquid port through which the agitated drilling fluid enters the bubbler enclosure from the sample enclosure and a gas port through which the bubbler air enters the sample enclosure, and the liquid inlet may be nearer to the liquid port than the gas port.

The agitator can include a shaft having a mixing portion shaped to facilitate agitation of the drilling fluid. A brushless DC motor may be rotatably coupled to the shaft.

The brushless DC motor may include a stator; a rotor directly coupled to a shaft extending from the brushless DC motor and rotatable relative to the stator in order to rotate the shaft, wherein rotation of the shaft results in the agitation. The bearings may be oversized relative to a typical off-the-shelf DC motor having a similar power rating so as to accommodate the length of the shaft.

A sealing portion may be disposed around the shaft between the DC motor and the sample enclosure. The sealing portion may have a first sealing element configured to prevent solid particulates from entering the DC motor and a second sealing element configured to prevent liquid from entering the DC motor. The first sealing element may be nearer to the sample enclosure than the second sealing element. The second sealing element may include two seals.

The apparatus may also include a disc disposed along the shaft to prevent the drilling fluid from entering the DC motor.

The apparatus may also include a gas sample conduit external to the gas trap and fluidly coupled to the gas sample outlet to transport the gas sample outside of the gas trap; and a heat trace thermally coupled to the gas sample conduit. Alternatively or additionally, the apparatus may also include a bubbler air conduit external to the gas trap and fluidly coupled to the bubbler air inlet to transport the pressurized bubbler air from outside of the gas trap to the gas trap; and a heat trace thermally coupled to the bubbler air conduit. The same heat trace may be thermally coupled to both the gas sample and bubbler air conduits.

The apparatus may also include a gas analyzer having a bubbler pump fluidly coupled to an air source and configured to output pressurized bubbler air, wherein the bubbler air inlet is fluidly coupled to the bubbler pump to receive the pressurized bubbler air.

According to another aspect, there is provided a method for liberating gases entrained in a drilling fluid. The method includes submerging a liquid inlet of a sample enclosure and a bubbler air outlet of a bubbler enclosure in the drilling fluid, wherein the sample and bubbler enclosures are fluidly coupled together such that they are equally pressurized and such that the drilling fluid agitated in the sample enclosure enters the bubbler enclosure; pressurizing the sample and bubbler enclosures using pressurized bubbler air such that the drilling fluid in the sample enclosure is at a level determined by the location of the bubbler air outlet; and agitating the drilling fluid within a sample enclosure to liberate the gases entrained therein.

The sample enclosure may be delineated by a sample enclosure wall comprising a sample enclosure wall portion and a shared wall portion. The bubbler enclosure may be delineated by a bubbler enclosure wall comprising a bubbler enclosure wall portion and the shared wall portion, and the sample enclosure and the bubbler enclosure may be fluidly coupled through the shared wall portion.

The shared wall portion may include a liquid port through which the agitated drilling fluid enters the bubbler enclosure from the sample enclosure and a gas port through which the bubbler air enters the sample enclosure, and the liquid inlet may be nearer to the liquid port than the gas port.

Agitation may be powered using a brushless DC motor.

The brushless DC motor may include a stator; a rotor directly coupled to a shaft extending from the brushless DC motor and rotatable relative to the stator in order to rotate the shaft, wherein rotation of the shaft results in the agitation. The bearings may be oversized relative to a typical off-the-shelf DC motor having a similar power rating so as to accommodate the length of the shaft.

The method may also include sealing the DC motor using a first sealing element configured to prevent solid particulates from entering the DC motor and a second sealing element configured to prevent liquid from entering the DC motor. The first sealing element may be nearer to the sample enclosure than the second sealing element. The second sealing element may include two seals.

The method may also include blocking splashing drilling fluid from entering the DC motor with a disc disposed along the shaft.

Gases liberated from the drilling fluid may be conveyed away from the sample enclosure using a heated gas sample conduit. Additionally or alternatively, the bubbler air may be conveyed to the bubbler enclosure using a heated bubbler air conduit.

According to another aspect, there is provided an apparatus for liberating gases from drilling fluid. The apparatus includes a sample enclosure having a liquid inlet and a gas sample outlet; an agitator disposed within the sample enclosure and configured to agitate drilling fluid located within the sample enclosure to liberate gases entrained in the drilling fluid so that the gases can exit through the gas sample outlet; and a brushless, DC motor rotatably coupled to the agitator to power the agitator.

The apparatus may also include a bubbler enclosure having a bubbler air inlet and a bubbler air outlet, and fluidly coupled to the sample enclosure such that the sample and bubbler enclosures are equally pressurized so that sufficiently pressurized bubbler air entering through the bubbler air inlet maintains the drilling fluid in the sample enclosure at a level determined by the location of the bubbler air outlet when the liquid inlet and the bubbler air outlet are both submerged in the drilling fluid, and such that agitated drilling fluid enters the bubbler enclosure from the sample enclosure.

The sample enclosure may be delineated by a sample enclosure wall comprising a sample enclosure wall portion and a shared wall portion. The bubbler enclosure may be delineated by a bubbler enclosure wall comprising a bubbler enclosure wall portion and the shared wall portion, and the sample enclosure and the bubbler enclosure may be fluidly coupled through the shared wall portion.

The shared wall portion can include a liquid port through which the agitated drilling fluid enters the bubbler enclosure from the sample enclosure and a gas port through which the bubbler air enters the sample enclosure. The liquid inlet can be nearer to the liquid port than the gas port.

The agitator may include a shaft having a mixing portion shaped to facilitate agitation of the drilling fluid, and the brushless DC motor may include a stator; a rotor directly coupled to a shaft extending from the brushless DC motor and rotatable relative to the stator in order to rotate the shaft, wherein rotation of the shaft results in the agitation. The bearings may be oversized relative to a typical off-the-shelf DC motor having a similar power rating so as to accommodate the length of the shaft.

There may also be a sealing portion disposed around the shaft and between the DC motor and the sample enclosure. The sealing portion may include a first sealing element configured to prevent solid particulates from entering the DC motor and a second sealing element configured to prevent liquid from entering the DC motor. The first sealing element can be nearer to the sample enclosure than the second sealing element. The second sealing element can comprise two seals.

A disc may be disposed along the shaft to prevent the drilling fluid from entering the DC motor.

The apparatus may also include a gas sample conduit external to the gas trap and fluidly coupled to the gas sample outlet to transport the gas sample outside of the gas trap; and a heat trace thermally coupled to the gas sample conduit. Additionally or alternatively, the apparatus may include a bubbler air conduit external to the gas trap and fluidly coupled to the bubbler air inlet to transport the pressurized bubbler air from outside of the gas trap to the gas trap; and a heat trace thermally coupled to the bubbler air conduit. The same heat trace may be thermally coupled to both the gas sample and bubbler air conduits.

According to another aspect, there is provided a method for liberating gases entrained in a drilling fluid. The method includes submerging a liquid inlet of a sample enclosure in the liquid; and agitating the drilling fluid within the sample enclosure to liberate the gases entrained therein by using a brushless DC motor.

The method may also include submerging a bubbler air outlet of a bubbler enclosure in the drilling fluid, and the sample and bubbler enclosures may be fluidly coupled together such that they are equally pressurized and such that the drilling fluid agitated in the sample enclosure enters the bubbler enclosure. The sample and bubbler enclosures may be pressurized using pressurized bubbler air such that the drilling fluid in the sample enclosure is at a level determined by the location of the bubbler air outlet.

The sample enclosure may be delineated by a sample enclosure wall comprising a sample enclosure wall portion and a shared wall portion, the bubbler enclosure may be delineated by a bubbler enclosure wall comprising a bubbler enclosure wall portion and the shared wall portion, and the sample enclosure and the bubbler enclosure may be fluidly coupled through the shared wall portion.

The shared wall portion can include a liquid port through which the agitated drilling fluid enters the bubbler enclosure from the sample enclosure and a gas port through which the bubbler air enters the sample enclosure, and the liquid inlet can be nearer to the liquid port than the gas port.

The brushless DC motor may include a stator; a rotor directly coupled to a shaft extending from the brushless DC motor and rotatable relative to the stator in order to rotate the shaft, wherein rotation of the shaft results in the agitation. The bearings may be oversized relative to a typical off-the-shelf DC motor having a similar power rating so as to accommodate the length of the shaft.

The method may also include sealing the DC motor using a sealing portion disposed around the shaft and between the DC motor and the sample enclosure. The sealing portion may include a first sealing element configured to prevent solid particulates from entering the DC motor and a second sealing element configured to prevent liquid from entering the DC motor. The first sealing element may be nearer to the sample enclosure than the second sealing element.

The method may also include blocking splashing drilling fluid from entering the DC motor with a disc disposed along the shaft.

Gases liberated from the drilling fluid may be conveyed away from the sample enclosure using a heated gas sample conduit. Alternatively or additionally, bubbler air may be conveyed to the bubbler enclosure using a heated bubbler air conduit.

The method may also include generating the bubbler air by using a pump located within a gas analyzer.

According to another aspect, there is provided a computer readable medium having encoded therein statements and instructions configured to cause a processor to execute a method as claimed in any of the foregoing aspects.

Directional terms such as "top", "bottom", "upwards", "downwards", "vertically" and "laterally" are used in the following description for the purpose of providing relative reference only, and are not intended to suggest any limitations on how any apparatus is to be positioned during use, or to be mounted in an assembly or relative to an environment.

Hydrocarbon deposits in the form of oil and gas deposits are often located underground. Wells are typically drilled in order to access these underground deposits. FIG. 1 depicts a drilling site 100 on which an exemplary oil well 106 is being drilled. A drilling rig 104 is used to rotationally drive a drill string 108 that has on one of its ends a drill bit 112. Rotation of the drill bit 112 through the earth drills the well 106. On the surface is a pump 102 that pumps drilling fluid down through the drill string 108, out through the drill bit 112, and up back to the surface through the annular region between the drill string 108 and the interior surface of the well 106; the path the drilling fluid travels from the pump 102 to the surface is indicated by the arrows in FIG. 1. Optionally, located along the drill string 108 and in the path of the drilling fluid is a measurement-while-drilling ("MWD") tool 110. The MWD tool 110 measures various downhole parameters, such as the resistivity of rock surrounding the drill bit 112 and the amount of gamma radiation encountered. The MWD tool 110 transmits the measured parameters to the surface by periodically interrupting the flow of the drilling fluid, which generates pressure signals indicative of the measured parameters that are transmitted to the surface through the drilling fluid that is being pumped down the drill string 108.

When the drilling fluid is forced out through the drill bit 112 and upwards through the annular region between the drill string 108 and the interior surface of the well 106, it comes into contact with the earth that is being drilled. If the earth contains hydrocarbons, a certain amount of these hydrocarbons dissolve into the drilling fluid and are conveyed back to the surface by the drilling fluid. At the surface, the hydrocarbons in the drilling fluid can be liberated from the drilling fluid and analyzed. A geologist can analyze the hydrocarbons to identify which hydrocarbons are contained in the drilling fluid and in what concentrations to determine the likelihood that the well 106 will be an oil or gas producing well. A higher proportion of "heavy hydrocarbons" (hydrocarbons containing one or two carbons, such as methane and ethane) relative to "light hydrocarbons" (hydrocarbons containing three or more carbons, such as butane, propane, and pentane) indicates that the well 106 is more likely to produce oil than natural gas; analogously, a higher ratio of light hydrocarbons to heavy hydrocarbons indicates that the well 106 is more likely to produce natural gas than oil.

The embodiments herein are directed at a method and apparatus for liberating the hydrocarbons from the drilling fluid and at a method and apparatus for analyzing the hydrocarbons dissolved in the drilling fluid. In particular, the following embodiments describe a gas trap that can be used to liberate the hydrocarbons from the drilling fluid in a gaseous form, and a gas analyzer that is capable of individually speciating the gaseous hydrocarbons such that the amount of each of methane, ethane, propane, and butane can be measured.

Gas Analyzer. Referring again to FIG. 1, a gas analyzer 114 is depicted in which a gas sample that is extracted from the drilling fluid is analyzed. Gas is extracted from the drilling fluid using a gas trap 700, as illustrated in FIGS. 1 and 7 to 12 and as discussed in more detail, below. Alternatively, a gas trap such as a Quantitative Gas Measurement (QGM) gas trap can be used. As described in further detail with respect to FIGS. 2 through 6, below, the gas analyzer 114 analyzes the gas sample and outputs measurement results to a data recording device 116 such as the Pason Electronic Drilling Recorder™. Optionally, the data recording device 116 takes into account the time lag it takes for the drilling fluid to reach the surface from the drill bit 112. For example, if the drill bit 112 is at a depth such that the drilling fluid requires five seconds to travel from the drill bit 112 to the surface and be analyzed, the data recording device 116 associates the measurement results not with the time at which the gas analyzer 114 outputs them, but at this time minus five seconds. The data recording device 116 is communicative via a network 118 with a data storage device 120 such as the Pason Datahub™. The data storage device 120 records measurement results transmitted to it from the data recording device 116 for subsequent access by a data access system 122 also in communication with the network 118, such as a personal computer. In addition to recording and storing data from the gas analyzer 114, the data recording and storage devices 116, 120 may also record and store data sent from other devices, such as the MWD tool 110 and various surface sensors (not shown). Notably, while in the present embodiment the drill string 108 includes the MWD tool 110, in alternative embodiments the MWD tool 110 is not present.

Figure 2:
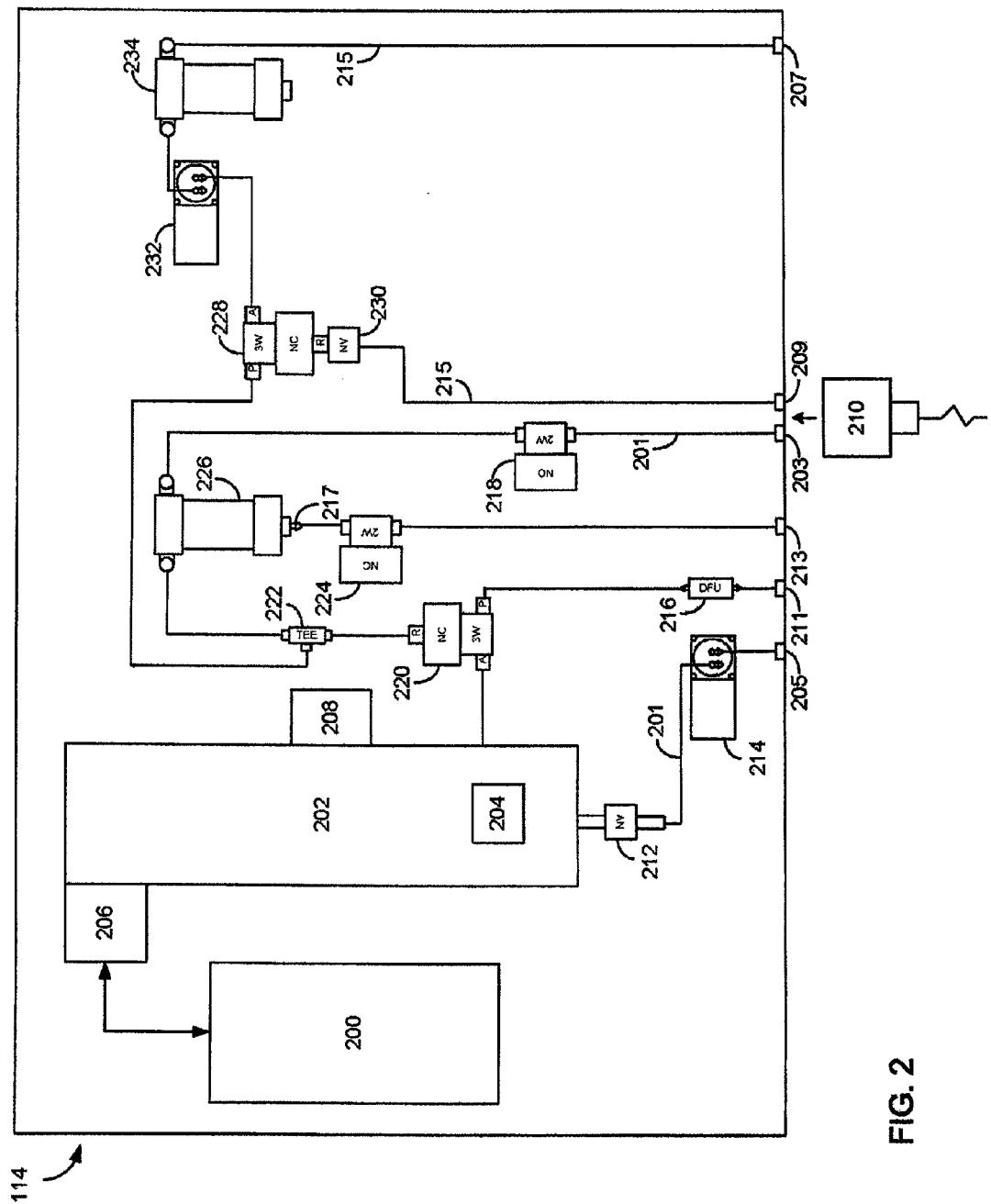
FIG. 2 is a schematic of the gas analyzer of FIG. 1.

Referring now to FIG. 2, there is depicted a schematic of the gas analyzer 114. The gas analyzer includes a hydrocarbon sensor 202 that performs measurements on the gas sample and that generates raw data in the form of absorption spectra that is analyzed during speciation of the hydrocarbons contained in the gas sample. As discussed in more detail in respect of FIGS. 4(a) and (b), below, the hydrocarbon sensor 202 passes light of a range of wavelengths through the gas sample. Depending on the composition of the gas sample, different amounts of the light at different wavelengths are absorbed, and the absorption spectra that the hydrocarbon sensor 202 measures varies.

Disposed on the hydrocarbon sensor 202 is a carbon dioxide ($CO_2$) sensor 204 that measures the amount of carbon dioxide in the gas sample while the hydrocarbons in the gas sample are being measured. A typical carbon dioxide sensor 204 is a Dynament™ carbon dioxide sensor, model number MSH-P/HCO2/5/V/P. The raw data that the hydrocarbon sensor 202 generates is amplified by a pre-amplifier/detector 206 (hereinafter a "preamp") that is electrically coupled to an electronics board 200. The electronics board 200 analyzes the raw data and outputs an analysis of what types of and how much of each type of hydrocarbon is present in the gas sample. In the present embodiment, the electronics board 200 outputs how much of each of methane, ethane, propane, butane and pentane is present in the gas sample. In alternative embodiments, the electronics board 200 can also output how much of each of the various isomers of pentane is present in the gas, how much of each of the various isomers of butane, such as i-butane and n-butane, is present in the gas, or may only output how much of a subset of methane, ethane, propane, butane and pentane is present in the gas (e.g.: only methane, ethane, propane and butane).

Figure 3:
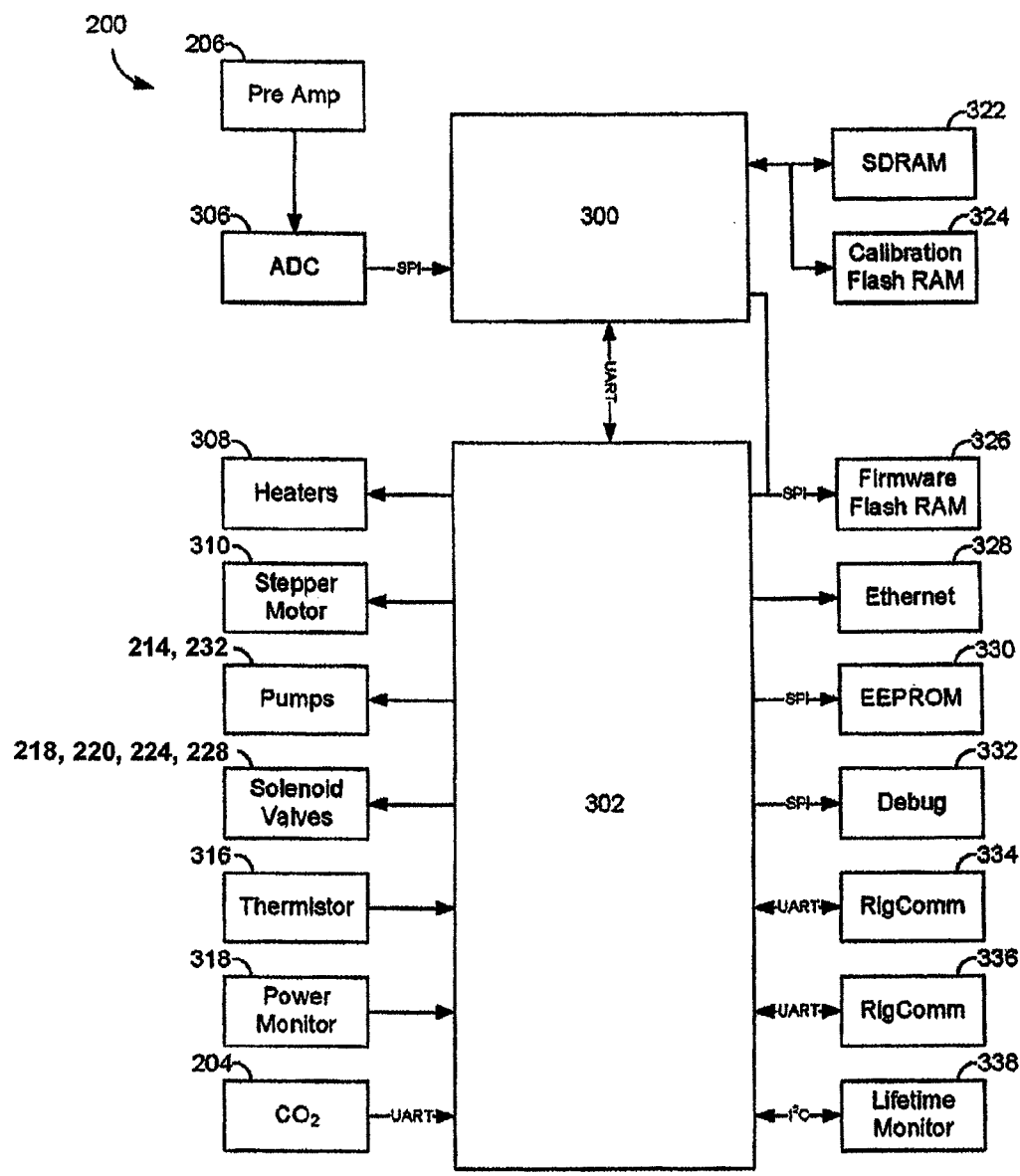
FIG. 3 is a block diagram of components disposed on an electronics board of the gas analyzer of FIG. 1.

Referring now to FIG. 3, there is depicted a block diagram of the preamp 206 connected to components that are on the electronics board 200. Measured absorption spectra that the hydrocarbon sensor 202 outputs are amplified by the preamp 206 and sent, in analog form, to an analog-to-digital converter (ADC) 306. The ADC 306 outputs digitized absorption spectra to a digital signal processor (DSP) 300. The DSP 300 is communicatively coupled to three types of memory: SDRAM 322, which is volatile memory used by the DSP 300 to store runtime data while the DSP 300 is operating; calibration flash RAM 324, which is non-volatile memory used to store calibration data generated when the gas analyzer 114 is run in a calibration mode, as discussed in more detail below; and firmware flash RAM 326, which is non-volatile memory used to store instructions and algorithms that the DSP 300 executes to analyze the measured absorption spectra and to speciate the hydrocarbons in the gas sample.

When analyzing the measured absorption spectra, the DSP 300 compares the measured absorption spectra with reference spectra stored in the calibration flash RAM 324. The reference spectra stored in the calibration flash RAM 324 includes absorption spectra for each of the hydrocarbons to be identified: methane, ethane, butane, propane and pentane. Examples of each of these reference spectra are pictured in FIGS. 6(a) to (e). Based on the degree to which the measured absorption spectra corresponds with the reference spectra stored in the calibration flash RAM 324, the DSP 300 speciates the gas sample by determining what proportion of each of methane, ethane, butane, propane and pentane is present in the gas sample. An example of how reference and measured absorption spectra are compared in order to result in identification of constituents of the gas sample is discussed in published patent application US 2010/0027004 (U.S. Ser. No. 12/427,485, filed Apr. 21, 2009), the entirety of which is hereby incorporated by reference herein. While in the present embodiment the reference spectra are stored in the calibration flash RAM 324, in alternative embodiments the reference spectra may instead be partially or entirely stored in the firmware flash RAM 328, or in any other type of suitable memory that is accessible to the DSP 300 while the DSP 300 is analyzing the measured absorption spectra.

Following speciation of the gas sample by the DSP 300, the DSP 300 transfers speciation results to a microcontroller 302. Like the DSP 300, the microcontroller 302 is connected to the firmware flash RAM 326, which in addition to storing instructions and algorithms for execution by the DSP 300, also stores instructions and algorithms for execution by the microcontroller 302. Also communicatively coupled to the microcontroller 302 are heaters 308 for maintaining the temperature of the gas analyzer 114 above freezing; a stepper motor 310, the actuation of which controls an optical filter 407 (not present in FIG. 3, but present and labelled in FIG. 4) contained within the hydrocarbon sensor 202 that controls what wavelength of light is directed through the gas sample; sample and bubbler pumps 214, 232 and solenoid valves 218, 220, 224, 228 used to control gas flow through the gas analyzer 114, as discussed in more detail below; a temperature sensor 316 that measures the current temperature within the gas analyzer 114, which provides feedback to the microcontroller 302 to better operate the heaters 308; a power monitor 318 for monitoring voltage levels within the gas analyzer 114 for diagnostic purposes; the carbon dioxide sensor 204; an Ethernet connection 328 that can be used to interface with the network 118; a serial connection such as a RigComm™ interface that can be used to communicate with the data recording device 116; a debug port 332 that can be used when troubleshooting the gas analyzer 114; electrically erasable programmable read only memory (EEPROM) used to store infrequently changed data, such as the serial number of the gas analyzer 114; and a lifetime monitor 338 that records the duration for which the gas trap 700 is used. As is indicated in FIG. 3, communication between the microcontroller 302 and the DSP 300, the RigComm™ interfaces 334, 336, and the carbon dioxide sensor 204 are done via a universal asynchronous receiver/transmitter (UART) embedded within the microcontroller 302; communication between the microcontroller 302 and the firmware flash RAM 326, the EEPROM 330, and the debug port 332 is done using a serial peripheral interface (SPI) bus; and communication between the microcontroller 302 and the lifetime monitor 338 is done using an inter-integrated circuit ($I^2C$) bus. The DSP 300 communicates with the firmware flash RAM 326 and the ADC 306 using a SPI bus.

The microcontroller 302 can configure the gas analyzer 114 to operate in multiple operating modes: calibration mode, zeroing mode, measurement mode, and two purge modes. In typical operation, the microcontroller 302 typically operates the gas analyzer 114 in measurement mode.

Measurement Mode. During measurement mode, the microcontroller 302 configures the pumps 214, 232 and solenoid valves 218, 220, 224, 228 to convey the gas sample from the gas trap 700 outside of the gas analyzer 114 to the hydrocarbon sensor 202 for analysis and, once analyzed, from the hydrocarbon sensor 202 back outside the gas analyzer 114 for discharge to atmosphere. The gas trap 700 is fluidly coupled to the gas analyzer at a sample inlet 203 via a gas sample conduit (not shown) contained within a tubing bundle 210. From the sample inlet 203, the gas sample travels along a sample flowline 201 through an open, two-way solenoid valve 218, and to a sample filter 226. The sample filter 226 removes from the gas sample any solid or liquid contaminants that may be present in the gas sample. An exemplary sample filter 226 is a model 360A filter housing fitted with a 30CS filter element, both from United Filtration Systems. After exiting the sample filter 226, the gas sample continues along the sample flowline 201 and passes through a three-way tee 222 to a closed, three-way solenoid valve 220. When the valve 220 is in the closed state, the gas sample is conveyed into the hydrocarbon sensor 202 via a gas inlet 402 (not labelled in FIG. 2, but labelled in FIG. 4(a)) in the hydrocarbon sensor 202, where the DSP 300 analyzes the gas sample by comparing absorption spectra measured by the hydrocarbon sensor 202 to reference absorption spectra stored in the calibration flash RAM 324.

Figure 4A:
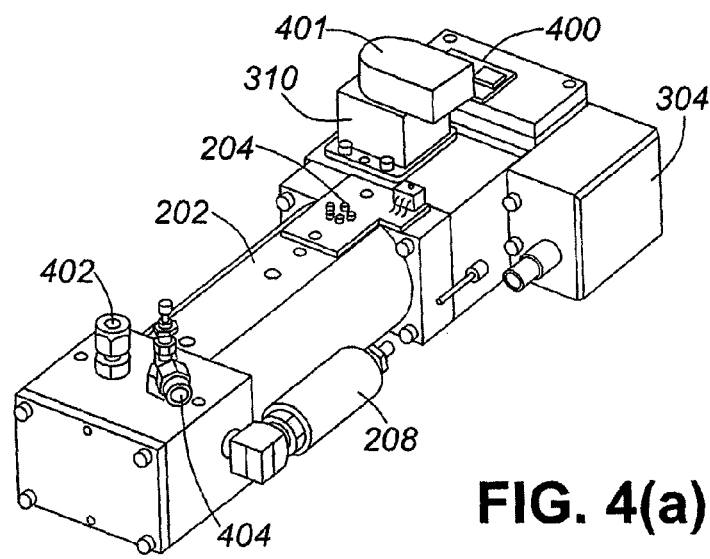
FIGS. 4(a) and (b) are perspective and sectional views, respectively, of a hydrocarbon sensor located in the gas analyzer of FIG. 1.

Following analysis, the gas sample exits the hydrocarbon sensor 202 through a gas outlet 404 in the hydrocarbon sensor 202 (not labelled in FIG. 2, but labelled in FIG. 4(a)). A needle valve 212 is attached to the gas outlet 404 that is manually adjustable to control the flow rate of the gas sample as it exits the hydrocarbon sensor 202. After passing through the needle valve, the gas sample continues along the sample flowline 201 through a sample pump 214 and exits the gas analyzer 114 through a sample outlet 205. The sample pump 214 pressurizes the entirety of the sample flowline 201 such that the gas sample is forced through the sample flowline 201 from the sample inlet 203 to the sample outlet 205.

While in measurement mode, air pressure is used to maintain a certain volume of drilling fluid in the gas trap 700. This volume of fluid is then agitated so as to liberate the hydrocarbons that form part of the gas sample that the gas analyzer 114 analyzes. In addition to hydrocarbons, other gases that may be liberated from the drilling fluid include carbon dioxide and hydrogen sulphide. The air used to maintain fluid volume in the gas trap 700 is "bubbler air" and is drawn in from an air source, such as the atmosphere, outside the gas analyzer 114 through a bubbler inlet 207 along a bubbler flowline 215 by virtue of pressurization caused by a bubbler pump 232 fluidly coupled along the bubbler flowline 215. The bubbler pump 232 draws the bubbler air along the bubbler flowline 215 and through a bubbler filter 234 that removes from the bubbler air any solid or liquid contaminants that may be present in the bubbler air. An exemplary bubbler filter 234 is a is a model 360A filter housing fitted with a 30CS filter element, both from United Filtration Systems. After being filtered, the bubbler air is pumped through the bubbler pump 232 and through a closed, three-way solenoid valve 228. When in the closed position, the bubbler air is directed out through a needle valve 230 attached to one of the ports of the three-way solenoid valve 228 that is adjustable so as to control the rate of flow of the bubbler air as it exits the gas analyzer 114 through a bubbler outlet 209. The bubbler outlet 209 is fluidly coupled to a bubbler air conduit (not shown) within the tubing bundle 210. The bubbler air conduit conveys the pressurized bubbler air to the gas trap 700, where it is used to prevent the drilling fluid in the gas trap 700 from exceeding a certain height, thereby also maintaining a certain volume of the drilling fluid. Optionally, a heat trace may be present in the tubing bundle 210 with the gas sample conduit and the bubbler air conduit to prevent the conduit from freezing when used in cold environments; the heat trace may be powered using a power supply (not shown) within the gas analyzer 114.

To allow the gas analyzer 114 to more accurately speciate hydrocarbons in the measurement mode, the gas analyzer 114 is calibrated in the calibration mode prior to entering the measurement mode.

Calibration Mode. Optionally, to enhance the accuracy of the gas analyzer 114, the gas analyzer 114 may be calibrated in the calibration mode prior to use in the measurement mode. In the calibration mode, the microcontroller 302 configures the pumps 214, 232 and the solenoid valves 218, 220, 224, 228 in the same manner as in the measurement mode. However, when in the calibration mode, one or more reference gas samples of known composition are fed to the gas analyzer 114 and speciated. If the gas analyzer 114 outputs speciation results that vary by more than a certain calibration threshold from the known compositions of the reference gas samples, the DSP 300 computes calibration factors that compensate for the difference between the speciation results and the known compositions of the reference gas samples. The calibration factors are stored in the calibration flash RAM 324 and are subsequently applied by the DSP 300 to adjust speciation results computed during the measurement mode to increase the accuracy of the readings that the gas analyzer 114 outputs.

Zeroing Mode. From time to time to help ensure speciation accuracy, the gas analyzer 114 can be zeroed. I.e., a gas sample having no hydrocarbons can be sent through the hydrocarbon sensor 202 and the gas analyzer 114 can be reset accordingly in order to mitigate any measurement drift that may have accrued over time. In the present embodiment, the gas analyzer 114 is zeroed prior to running the calibration mode for the first time, and is also zeroed from time to time thereafter.

In zeroing mode, the microcontroller 302 actuates the solenoid valve 220 such that it is in an opened state; the remainder of the solenoid valves 218, 224, 228 are in the same state as described above with respect to the measurement and calibration modes. When the solenoid valve 220 is in the opened state, suction generated by the sample pump 214 draws atmospheric air in from a zeroing air inlet 211; this atmospheric air is hereinafter referred to as "zeroing air". The zeroing air is sucked through a disposable filter unit (DFU) 216, which filters from the zeroing air any hydrocarbons that it may contain. Following filtering, the zeroing air passes through the solenoid valve 220, is analyzed by the hydrocarbon sensor 202, and then is pumped out of the gas analyzer 114 via the sample outlet 205.

Purge Modes. The microcontroller 302 is capable of initiating two types of purging: a "low pressure purge" that removes debris that has collected in the sample filter 226, and a "high pressure purge" that clears debris that has collected in the sample flowline 201 and that is impeding gas sample collection and analysis. Both the high pressure and low pressure purges are typically periodically initiated while the gas analyzer 114 is operating in measurement mode.

To initiate the low pressure purge, the microcontroller 302 actuates the two-way solenoid valve 224 from a closed into an opened position. When open, the solenoid valve 224 fluidly couples a drain 217 of the sample filter 226 to a discharge outlet 213 through which waste can exit the gas analyzer 114. This allows debris that has collected in the sample filter 226 to pass through the solenoid valve 224 and to exit the gas analyzer 114 via the discharge outlet 213. During typical operation, the microcontroller 302 initiates the low pressure purge periodically while the gas analyzer 114 is operating in the measurement mode. For example, the gas analyzer 114 may initiate the low pressure purge once every 120 minutes, during which time the solenoid valve 224 is held open for 20 to 30 seconds.

To initiate the high pressure purge, the microcontroller 302 uses the bubbler pump 232 to build up pressure within the sample filter 226. In order to do this, the microcontroller 302 puts the valves 218 and 224 into the closed state, and puts the valves 220 and 228 into the open state while the bubbler pump 232 is operating. The bubbler pump 232 consequently pumps bubbler air from the bubbler inlet 207, through the valve 228, through the tee 222, and into the sample filter 226, which acts as a pressure reservoir. Because both of the valves 218 and 224 are in the closed state, pressure builds up within the sample filter 226. After a certain period of time, for example 30 seconds, the microcontroller 302 opens the valve 218 and a burst of pressurized air is discharged from the sample filter 226 and rushes through the sample flowline 201 and out of the sample inlet 203, thereby clearing the sample flowline 201.

In contrast to the low pressure purge, the microcontroller 302 does not initiate the high pressure purge based on time. Instead, the microcontroller 302 monitors readings generated by a pressure sensor 208 that is affixed to the hydrocarbon sensor. The pressure sensor 208 measures the pressure that the sample pump 214 must overcome in order to intake air through either of the zeroing air inlet 211 and the sample air inlet 213. When the pressure required to intake air through either of the inlets 211, 213 exceeds a certain threshold, such as around 5 kPa, the microcontroller 302 infers that a blockage in the flowlines attached to the inlets 211, 213 is preventing proper airflow and consequently initiates the high pressure purge. The high pressure purge can also be triggered manually by, for example, having an operator of the gas analyzer 114 actuate a switch on the data recording device 116 that is electrically coupled to the microprocessor 302.

Figure 4B:
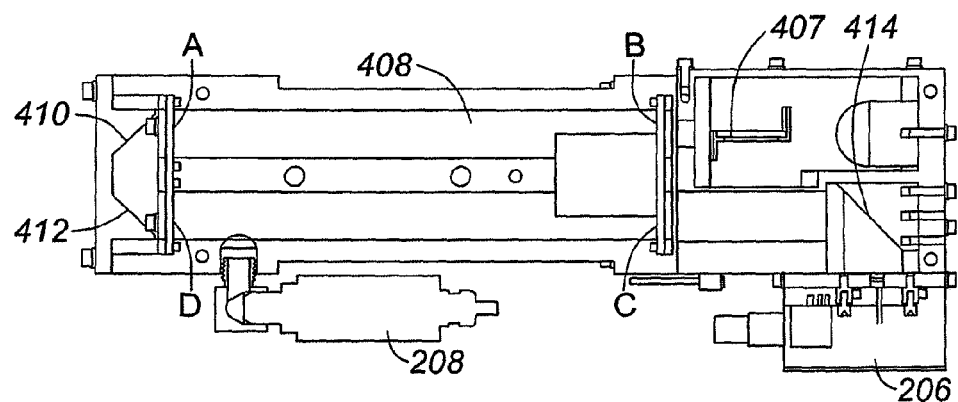

Referring now to FIGS. 4(*a*) and (*b*), there are depicted perspective and sectional views, respectively, of the hydrocarbon sensor 202. Located at one end of the sensor 202 are the gas inlet 402 and gas outlet 404 through which the gas sample enters and exits the hydrocarbon sensor 202, respectively, and which are both located along and fluidly coupled to the sample flowline 201. After entering the hydrocarbon sensor 202, the gas sample enters a U-shaped gas cell 408. The gas sample enters the gas cell 408 at point A in FIG. 4(*b*) and travels sequentially through points B, C and D prior to exiting the gas cell 408 and the hydrocarbon sensor 202 through the gas outlet 404. While the gas sample is resident in the gas cell 408, an infrared emitter 400 generates infrared light in the near infrared range, which is directed into the gas cell 408. The infrared light travels along one branch of the gas cell 408 from point B to point A, reflects off of a first reflector 410 and then a second reflector 412, and travels in an opposite direction along a second branch of the gas cell 408 from point D to point C; the distance the infrared light travels from point B to point A and from point D to point C is the "path length" of the infrared light; in the depicted embodiment, the distance from point A to point D is not included in the "path length" because the infrared light is not passing through the gas sample when travelling from point A to point D. The microcontroller 302 actuates the stepper motor 310, which is connected to the optical filter 407 located between the infrared emitter 400 and the gas cell 408. A positional encoder 401 monitors the position of the stepper motor 310 and reports the position to the microcontroller 302. Actuation of the stepper motor 310 results in the optical filter 407 allowing only a certain wavelength of the infrared light to pass through the gas sample at any one time; continued actuation of the stepper motor 310 irradiates the gas sample with light over a select range of wavelengths. In the present embodiment the wavelengths used are centred on about 1.70 µm and range from about 1.55 µm to 1.85 µm, although in alternative embodiments different wavelength ranges can be used. For example, in an alternative embodiment the wavelengths may be selected from elsewhere within the near infrared range, which extends from about 0.80 µm to about 2.50 µm. Part of the infrared light is absorbed by the hydrocarbons in the gas sample present in the gas cell 408. The light that is not absorbed reflects off a third reflector 414 and is directed into the preamp 206, where the absorbed spectra is converted into analog form and sent to the ADC 306 for analysis by the DSP 300 and the microcontroller 302. While the gas sample is being irradiated, the pressure sensor 208 measures the pressure level within the gas cell 202 and the carbon dioxide sensor 204 measures the level of carbon dioxide of the gas sample. In the depicted embodiment, the infrared emitter 400 is an incandescent infrared light source; in alternative embodiments, however, the light source may be a coherent light source of one or more frequencies. For example, the light source may be a tunable laser diode.

Using relatively short wavelengths centred on about 1.70 µm to irradiate the sample gas is advantageous compared to using relatively long wavelengths centred on about 3.30 µm, for example, because linearity of absorption is generally greater at 1.70 µm than at 3.30 µm. "Linearity of absorption" refers to the degree to which absorption of infrared radiation linearly correlates with the concentration of hydrocarbons in the gas sample. For example, assuming perfectly linear absorption and for any given path length through the gas sample, when the gas sample has a 1% concentration of hydrocarbons absorption of the infrared radiation will be exactly one half the absorption when the gas sample has a 2% concentration of hydrocarbons.

The greater the linearity of absorption, the easier it is to perform at least some of the calculations that are done during operation of the gas analyzer 114 in both calibration and measurement modes. For example, during calibration mode the calibration factor that is determined at one hydrocarbon composition is extrapolated to determine calibration factors at other hydrocarbon compositions; this extrapolation is generally less computationally intensive and consequently easier to perform when linearity of absorption is relatively high than when linearity of absorption is relatively low, such as when wavelengths centred on about 3.30 µm are used. Additionally, when linearity of absorption is relatively high, extrapolation accuracy can also be increased relative to when linearity of absorption is relatively low, resulting in more accurate calculations being performed during the calibration and measurement modes.

However, beneficially, when wavelengths centred on about 3.30 µm are used, total absorption per unit volume of the gas sample is higher than when wavelengths centred on about 1.70 µm are used. Consequently, when wavelengths centred on about 3.30 µm are used, a shorter path length can be used when generating measurement data than when using wavelengths centred on about 1.70 µm, and the smaller the hydrocarbon sensor 202 that can be manufactured. In the present embodiment, in order to obtain the benefits conferred by increased linearity, infrared radiation centred on about 1.70 µm is used and the hydrocarbon sensor 202 is sized large enough and configured with the first and second reflectors 410, 412 such that the path length is long enough for useful measurement data to be generated.

Figure 5A:
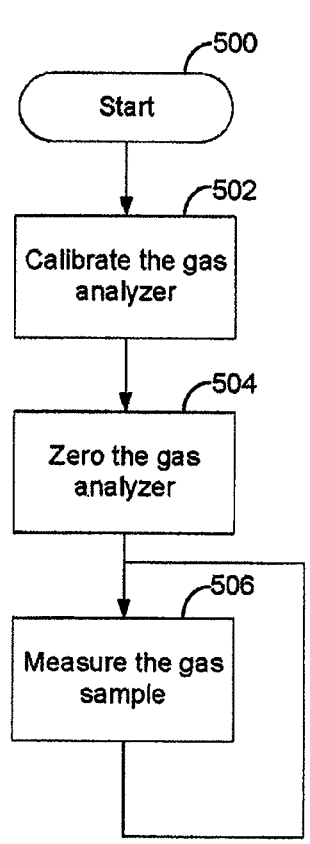
FIGS. 5(a) and (b) are flowcharts describing a method of operating the gas analyzer of FIG. 1, according to a second embodiment.
Figure 5B:
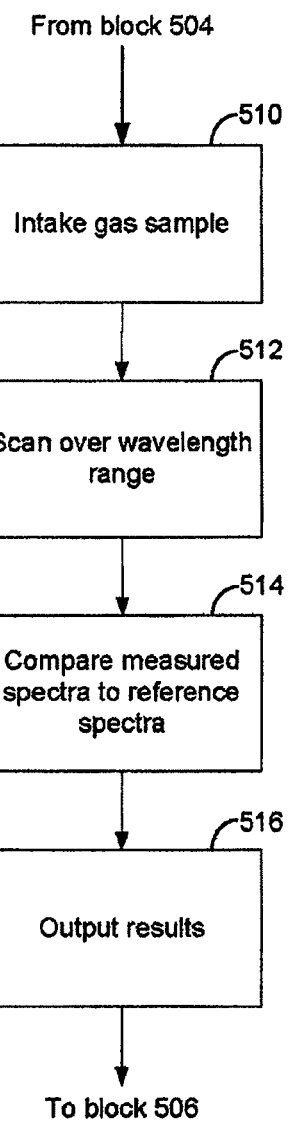
Figure 6A:
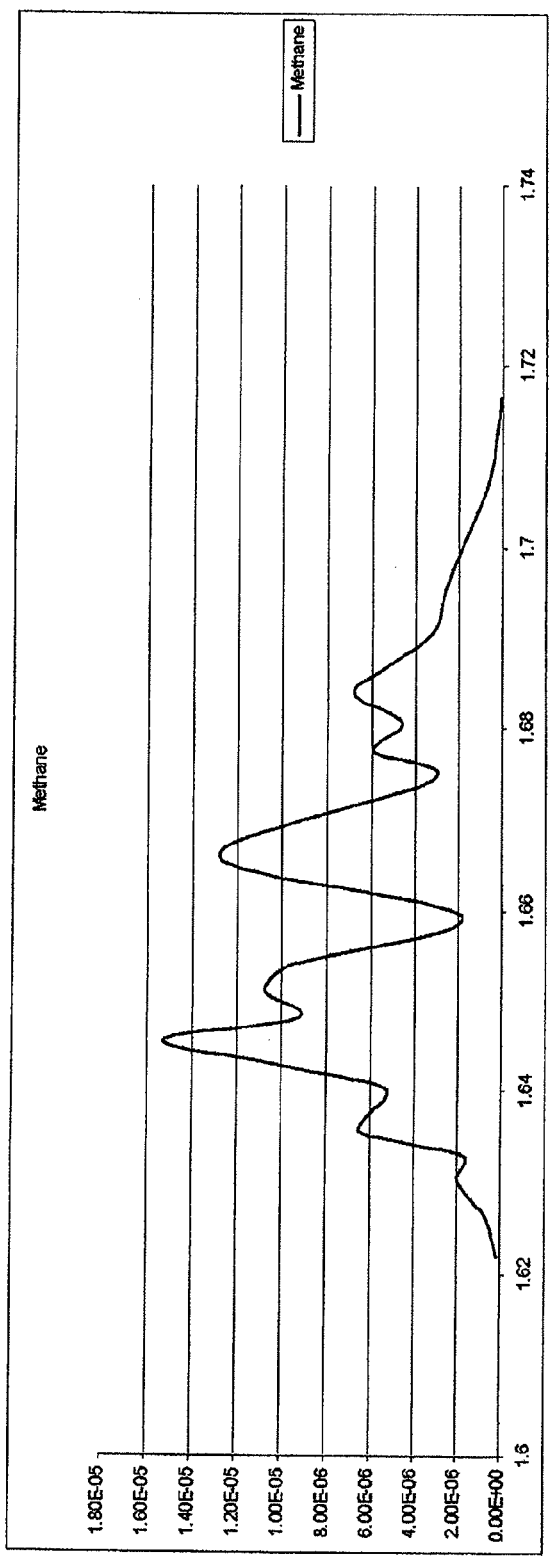
FIGS. 6(a) to (e) are exemplary absorption spectra for each of methane, ethane, propane, butane and pentane, respectively, measured during operation of the gas analyzer of FIG. 1.
Figure 6B:
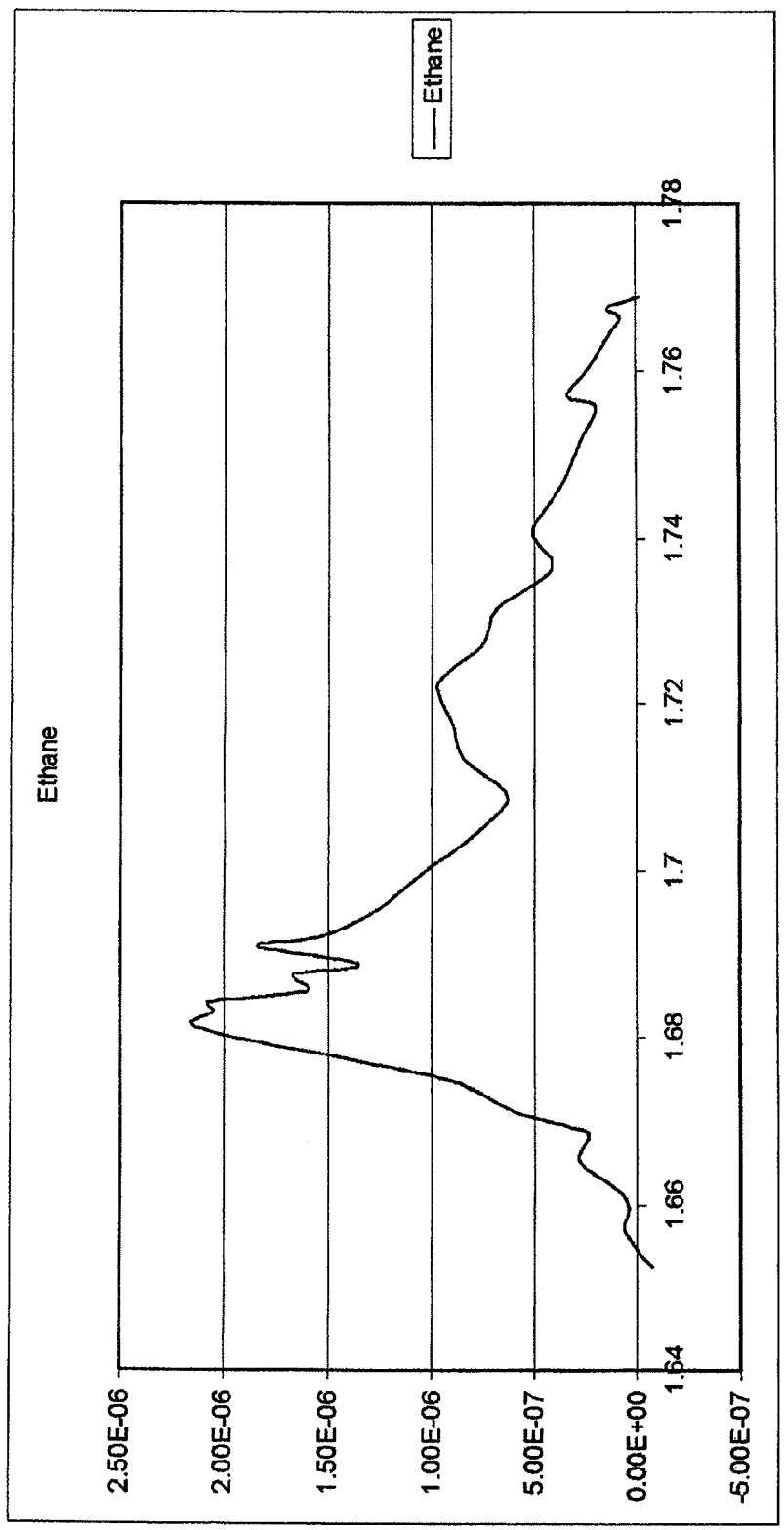
Figure 6C:
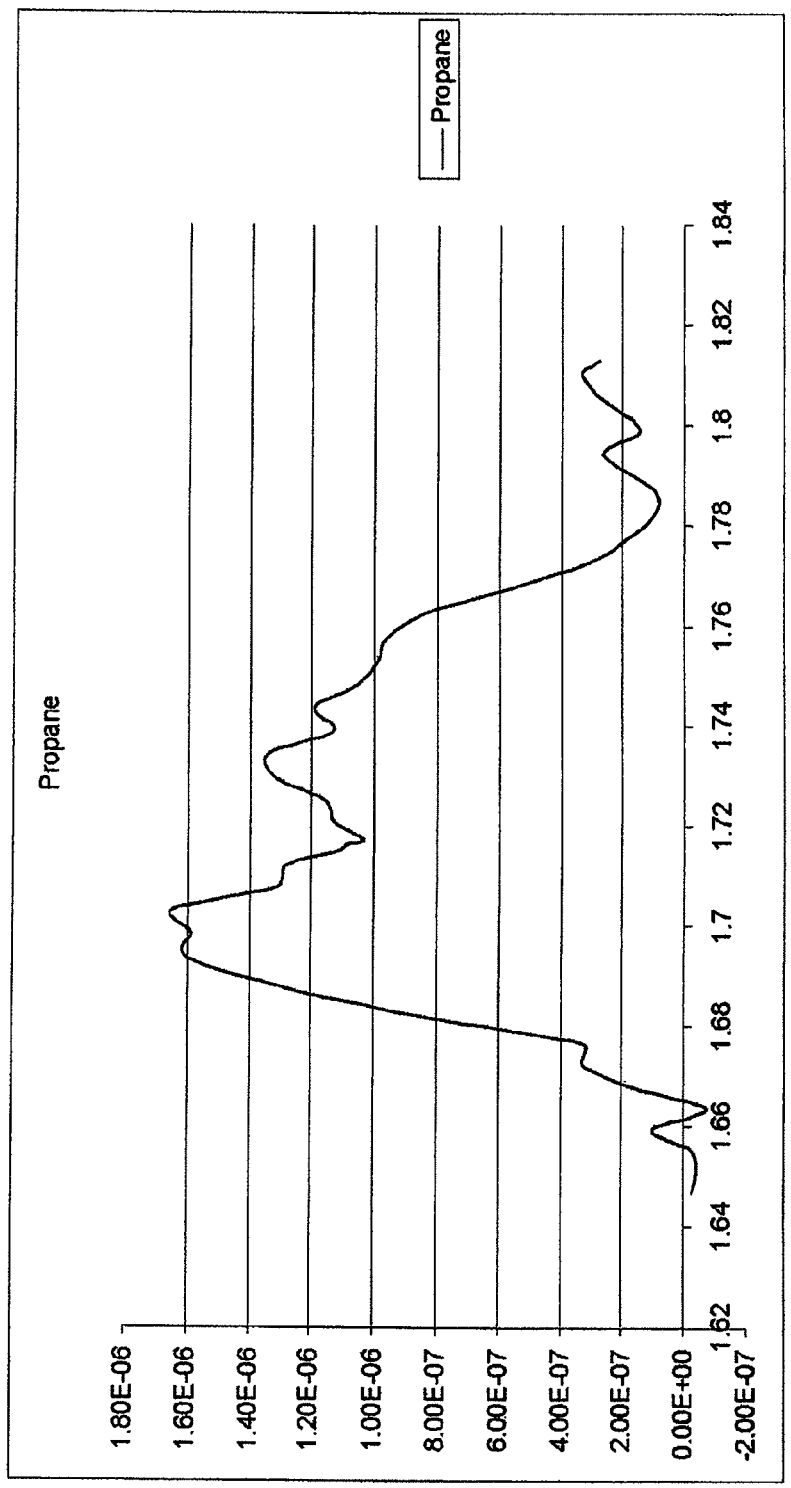
Figure 6D:
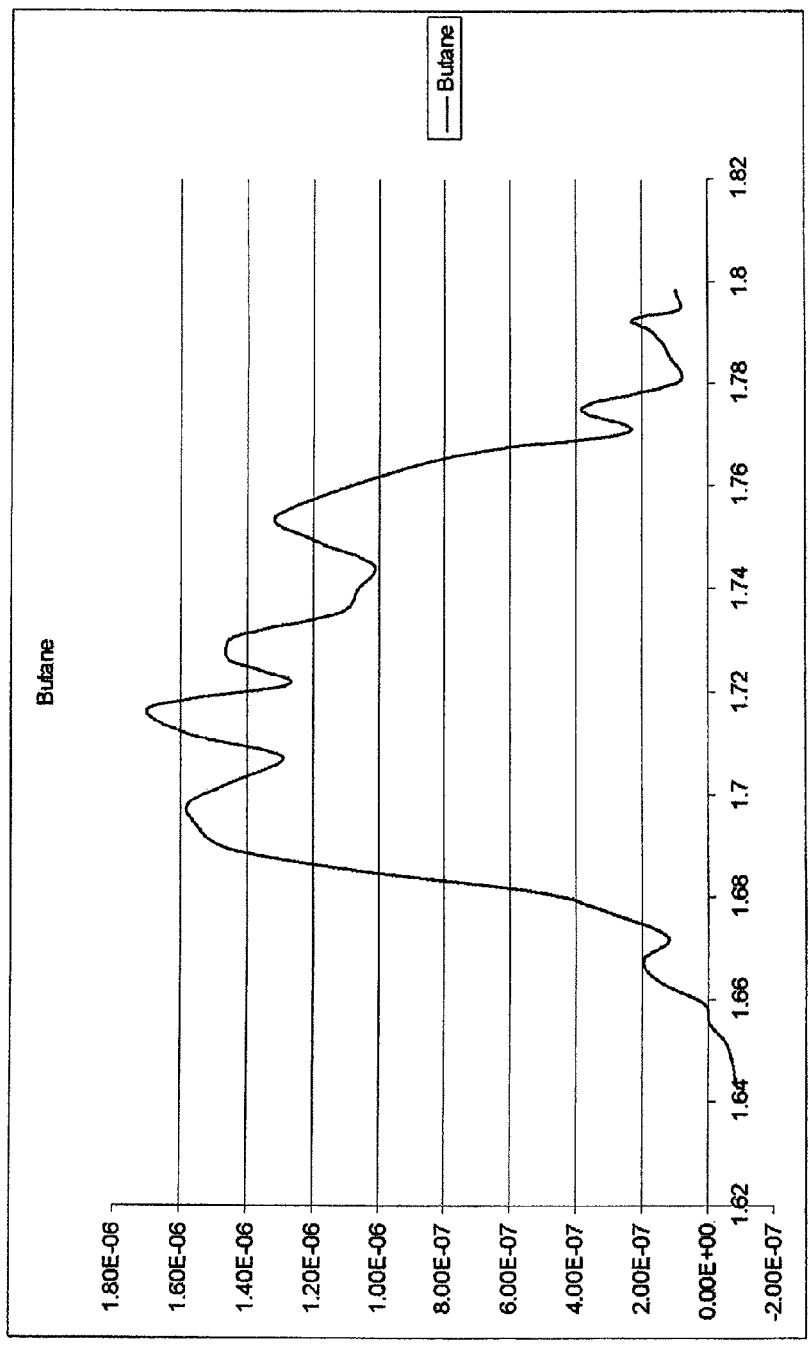
Figure 6E:
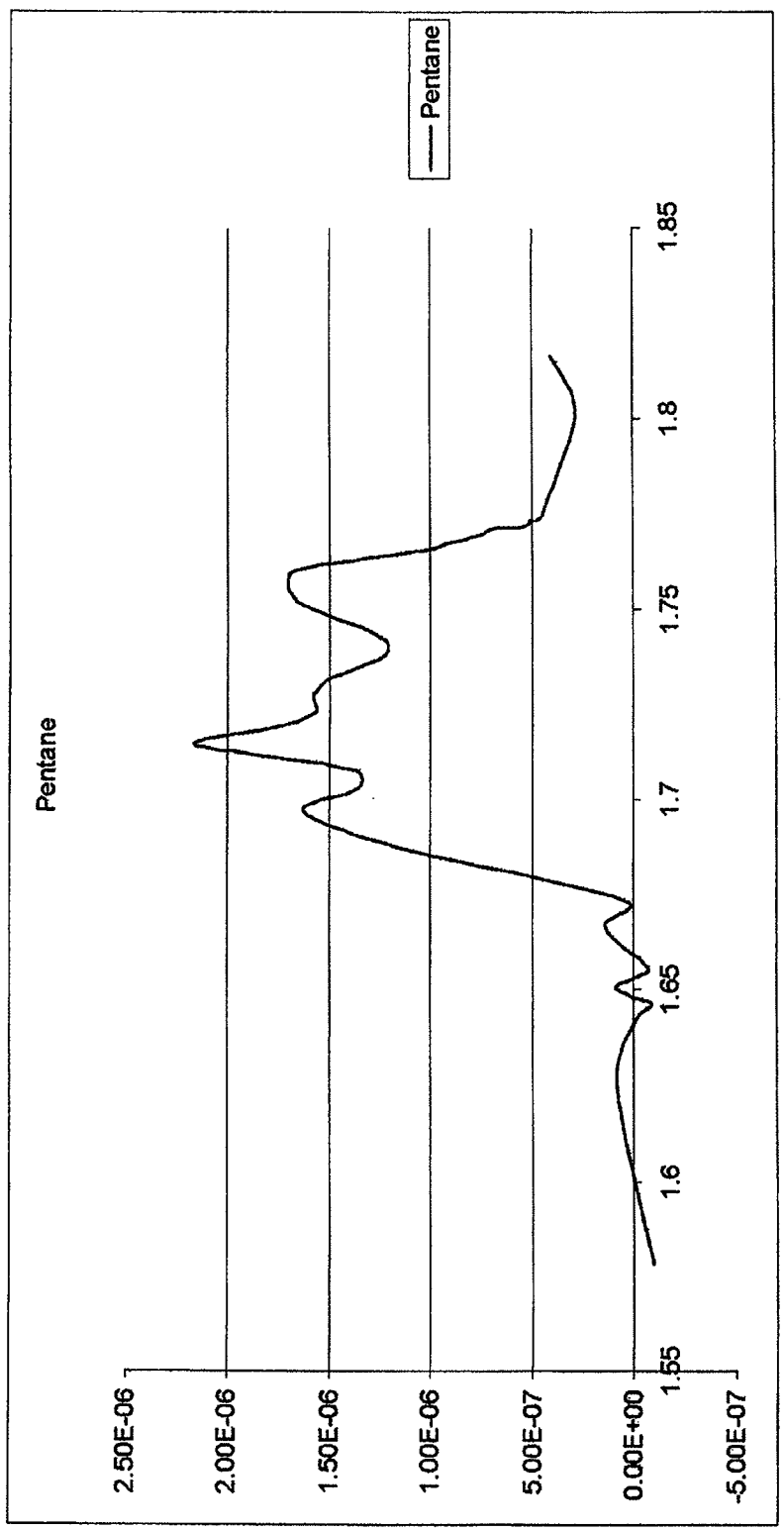

Referring now to FIGS. 5(*a*) and (*b*), there are depicted embodiments of methods for operating the gas analyzer 114. In FIG. 5(*a*), operation of the gas analyzer 114 begins at block 500; block 500 can correspond, for example, with activation of the gas analyzer 114. The microcontroller 302 then cycles the gas analyzer 114 through the calibration and zeroing modes, respectively, at blocks 502 and 504. At block 506, the microcontroller 302 causes the gas analyzer 114 to enter the measurement mode. In the present embodiment, measurement is done on a continuous basis as gas is continuously pumped through the hydrocarbon sensor 202. In the present embodiment the gas sample is pumped through the hydrocarbon sensor at a rate of about 800 cc/minute, although alternative flow rates can also be used. In an alternative embodiment, measurement may be done on a batch basis. I.e., the gas analyzer 114 may intake one gas sample of a certain volume, analyze it, and expel it prior to taking in another gas sample for analysis.

FIG. 5(*b*) illustrates how the gas analyzer 114 measures the gas sample. At block 510, the gas sample is drawn in through the sample inlet 203 and pumped along the sample flowline 201 until it reaches the hydrocarbon sensor 202. Once at the hydrocarbon sensor 202, the microcontroller 302 activates the infrared emitter 400, which emits infrared light that is filtered by the optical filter 407. As the passband of the optical filter 407 is being continuously adjusted by the rotating stepper motor 310, the gas sample is irradiated over a range of infrared light (block 512). At block 514, the measured absorption spectra detected and amplified by the preamp 206 are transmitted to the DSP 300, which compares the measured absorption spectra to the reference absorption spectra stored in the calibration flash RAM 324. The degree of correlation between the two spectra determines how many of each of methane, ethane, butane and propane is present in the gas sample. How much of each hydrocarbon is then sent to the microcontroller 302, which at block 516 can output the analysis results over an Ethernet or serial connection to the data recording device 116. Optionally, the microcontroller 302 may also compute and out various ratios potentially useful for geologists. The microcontroller 302 may, for example, compute any one or more of the balance ratio ($[(C1+C2)/(C3+C4+C5)]$), the wetness ratio ($[(C2+C3+C4+C5)/(C1+C2+C3+C4+C5)]*100$), the character ratio ($[(C4+C5)/C3]$), or compute the ratio of light hydrocarbons to total hydrocarbons (the sum of light and heavy hydrocarbons).

Beneficially, the gas analyzer 114 is able to speciate the hydrocarbons in the gas sample continuously and in real time, which allows the gas analyzer 114 to output speciation results quickly. Also beneficially, the gas analyzer 114 does not require carrier air to dilute the gas sample prior to measurement or to otherwise facilitate speciation, which simplifies construction of the gas analyzer 114. I.e., the gas analyzer 114 does not mix carrier air with the gas sample to reduce the concentration of the hydrocarbons in the gas sample to a level such that the hydrocarbon sensor 202 can analyze them; instead, the hydrocarbon sensor 202 is able to directly analyze whatever concentration of hydrocarbons is present in the gas sample directly as liberated from the drilling fluid. Any air that mixes with the gas sample occurs in relatively minimal volumes and does so incidentally as a result the suction that draws the gas sample into the gas analyzer 114 from the gas trap 700. This contrasts with some conventional systems used to speciate hydrocarbons, such as gas chromatographs, which intentionally introduce relatively large volumes of carrier air to a gas sample in order to facilitate speciation.

Gas Trap. As discussed above, the gas analyzer 114 obtains the gas sample from the gas trap 700. Known gas traps typically use either an air motor that is powered using pressurized rig air or an AC induction motor in order to agitate the drilling fluid. Each of these motors has drawbacks. For example, merely operating the air motor does not inherently generate feedback that allows the motor operator to know the motor's speed. Instead, in order to measure the speed of the air motor sensors are typically installed and monitored. Additionally, air motors utilize voltage to pressure converters that can be difficult to precisely control, which accordingly can make it difficult to precisely control the speed of the air motor. Furthermore, on a drilling rig the air motor is fluidly coupled to an air compressor that powers any pneumatics on the rig; the air provided by this air compressor is called "rig air". Depending on the number of devices powered using rig air, obtaining sufficient air pressure from the air compressor in order to run the air motor can be a problem. Another problem related to air motors is that in order to prevent the rig air from freezing, contaminants such as one or both of alcohol and antifreeze may be added to the rig air; other contaminants, such as solid particulates, may also be in the rig air. These contaminants can lead to problems such as corrosion that eventually wreck the air motor.

One drawback of the AC induction motor is its relative inefficiency, which results in its generating a significant amount of waste heat during operation. Consequently, a cooling fan is typically used in conjunction with the AC induction motor, which can be problematic on a drilling rig on which drilling fluid is splashing and interfering with the cooling fan's operation. Additionally, the rate of rotation of the AC induction motor varies with the frequency of the electrical signal that drives the motor. This can result in the speed of the AC induction motor varying with its location of use, as some countries transmit AC power at 50 Hz while others transmit power at 60 Hz. Furthermore, it can be difficult to obtain speed feedback from the AC induction motor; the motor is consequently often run as part of an open loop system in which the motor is simply, and sometimes incorrectly, presumed to be operating at a certain speed regardless of its actual performance. AC induction motors that are used in gas traps are also typically relatively heavy, commonly weighing about 30 lbs.

Additionally, it is beneficial to make the footprint of the gas trap relatively small. After the drilling fluid is pumped from the well, it is deposited into a shaker box. The shaker box acts as a reservoir that stores the drilling fluid prior to and while the drilling fluid is being agitated within the gas trap. The gas trap is immersed in the drilling fluid that is in the shaker box and liberates entrained gases from the drilling fluid in order to generate the gas sample that the gas analyzer 114 analyzes. Because shaker boxes are constrained in size, making the footprint of the gas trap relatively small increases the range of shaker boxes with which the gas trap can be used.

The embodiments of the gas trap 700 depicted in FIGS. 7 through 12 utilize a configuration that facilitates the gas trap 700 having a relatively small footprint, and that utilizes a brushless DC motor in lieu of an AC induction motor or an air motor. Doing so helps to ameliorate the problems associated with using air motors or AC induction motors, and facilitates mounting of the gas trap 700 on to shaker boxes of various sizes.

Figure 7:
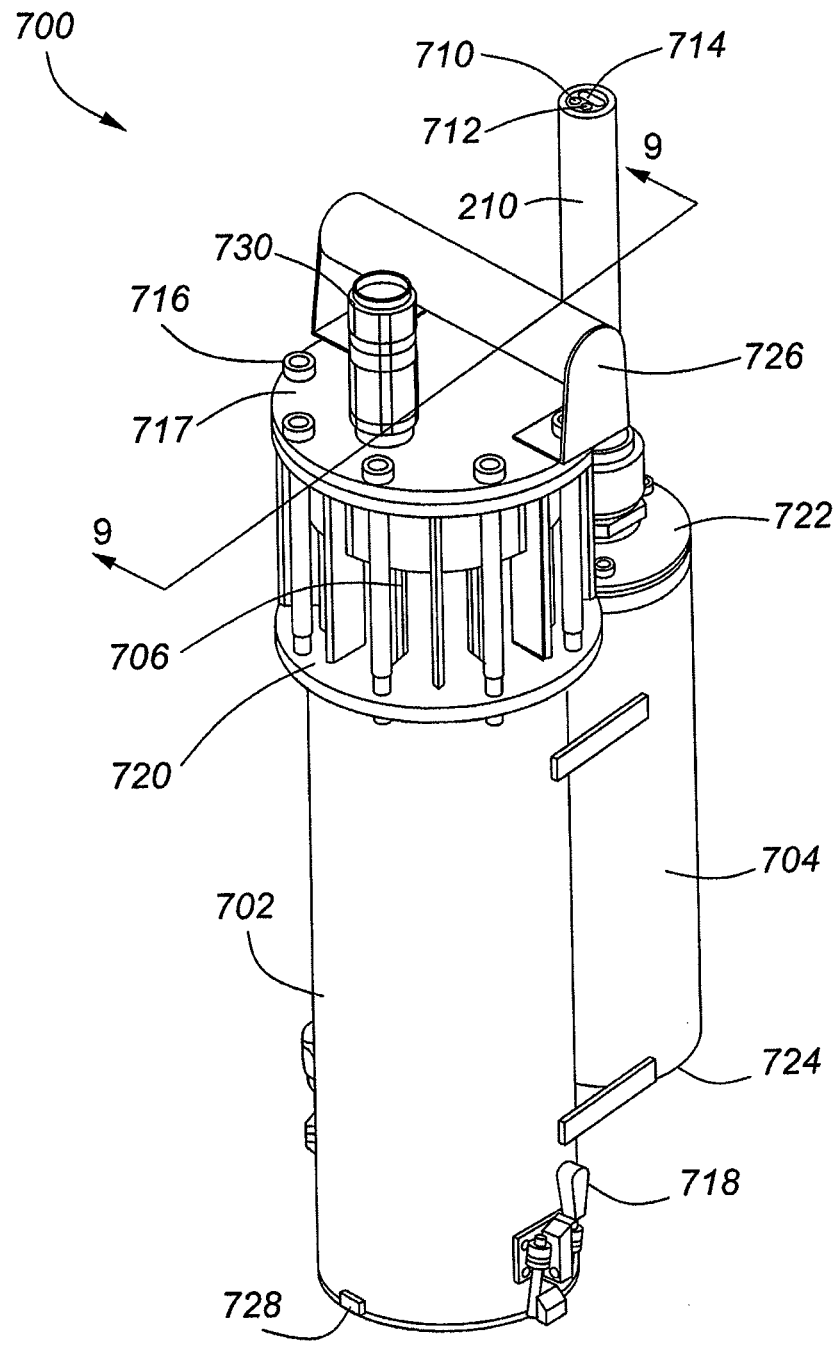
FIG. 7 is a perspective view of a gas trap according to a second embodiment.
Figure 8:
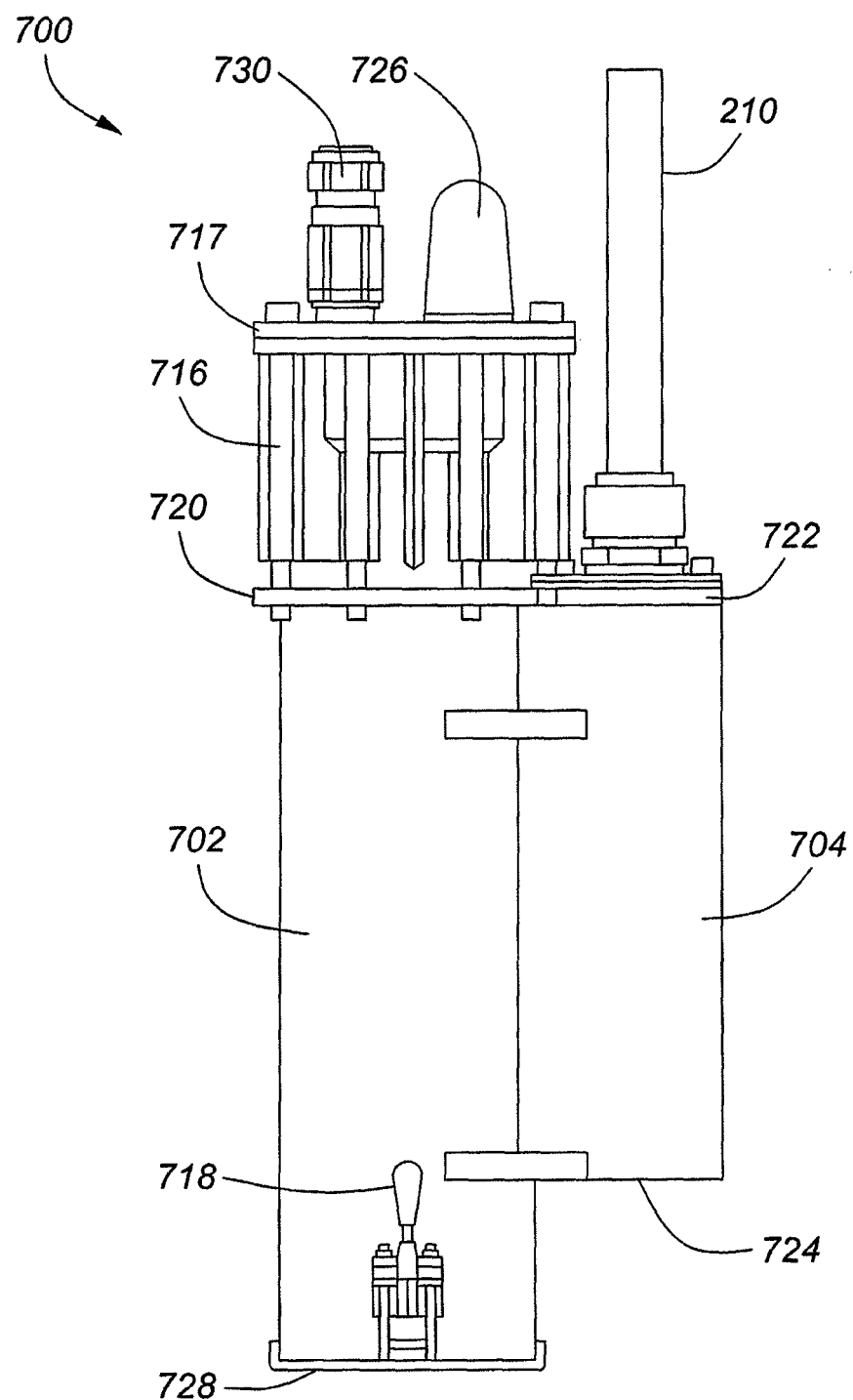
FIG. 8 is a front elevation view of the gas trap of FIG. 7.
Figure 9:
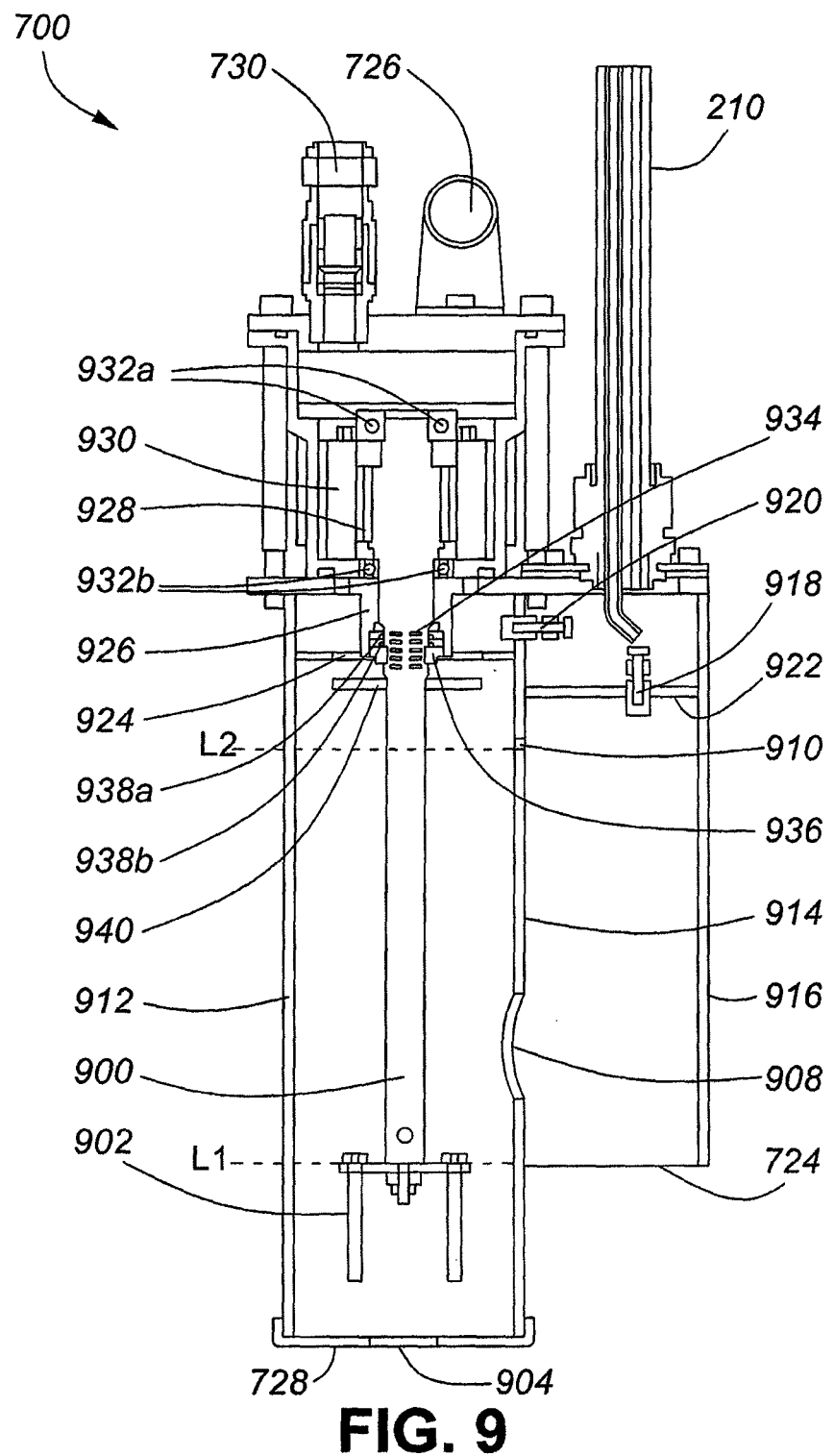
FIG. 9 is a sectional view of the gas trap of FIG. 7, taken along line 9-9 of FIG. 7.
Figure 10:
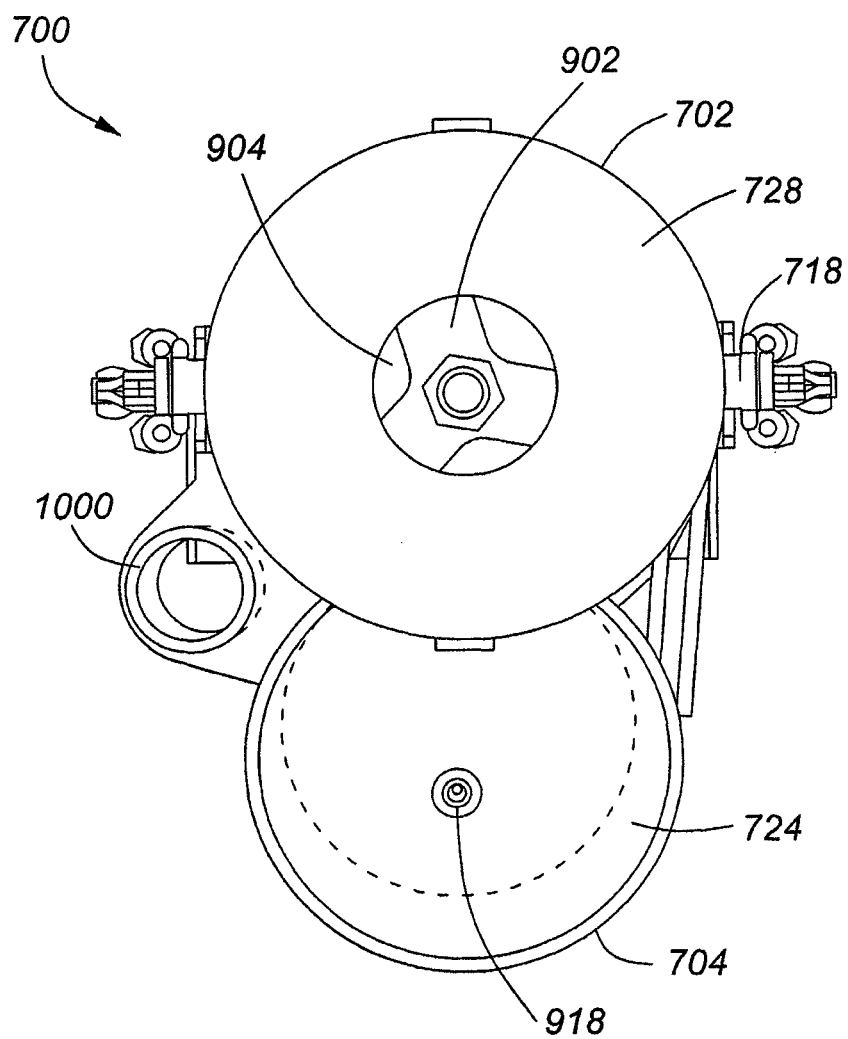
FIG. 10 is a bottom plan view of the gas trap of FIG. 7.
Figure 11:
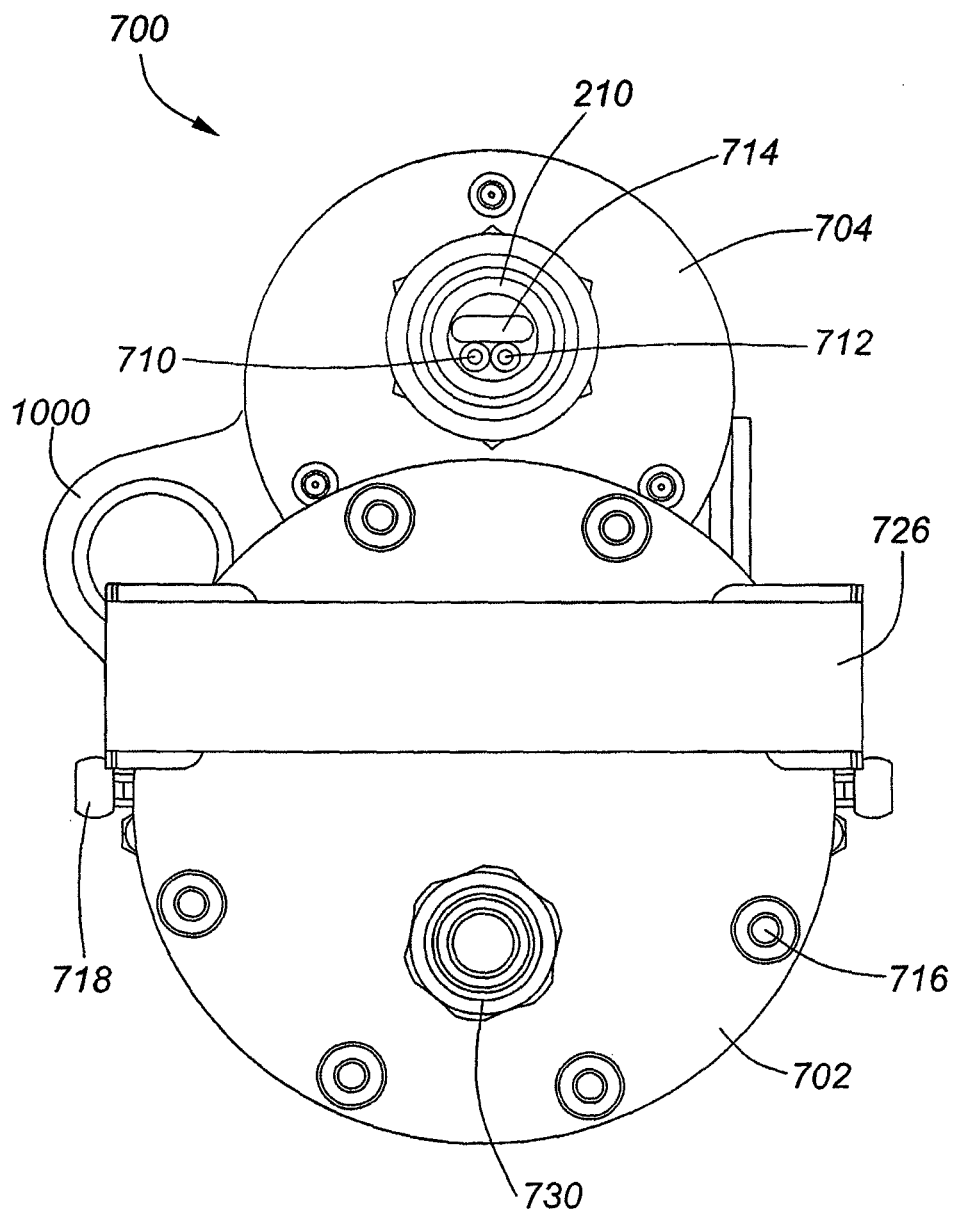
FIG. 11 is a top plan view of the gas trap of FIG. 7.
Figure 12:
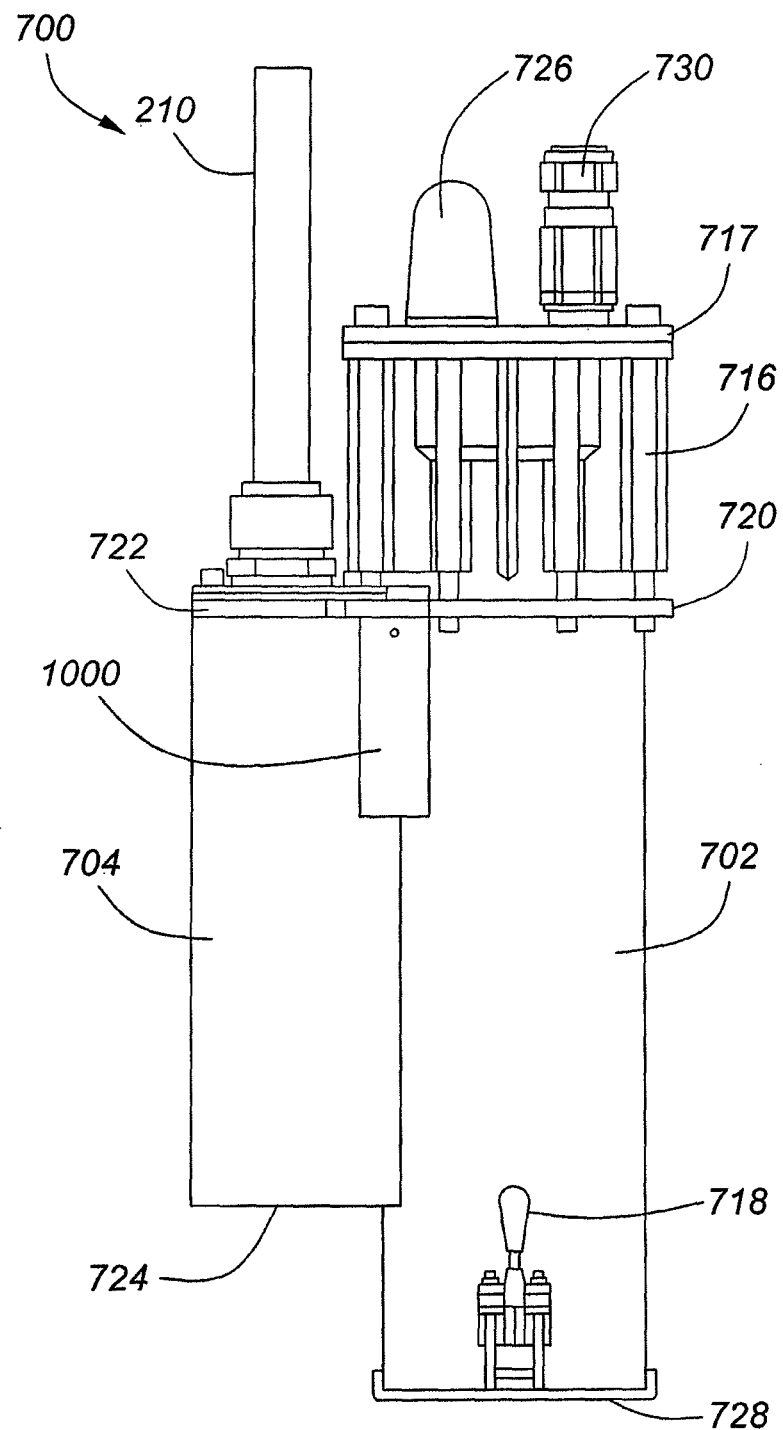
FIG. 12 is a rear elevation view of the gas trap of FIG. 7.

Referring now to FIGS. 7 to 12, there is depicted a gas trap 700 according to a first embodiment. FIG. 7 is a perspective view of the gas trap 700; FIG. 8 is a front elevation view of the gas trap 700; and FIG. 9 is a sectional view of the gas trap 700 along line 9-9 of FIG. 7; FIG. 10 is a bottom plan view of the gas trap 700; FIG. 11 is a top plan view of the gas trap 700; and FIG. 12 is a rear elevation view of the gas trap 700. The gas trap 700 includes two adjacent enclosures: a sample enclosure 702 and a bubbler enclosure 704. At the bottom of the sample enclosure 702 is a lid 728 that is secured to the sample enclosure 702 via a pair of latches 718. Disposed in the lid 728 is a liquid inlet 904 (visible in FIGS. 9 and 10) through which drilling fluid may enter the sample enclosure 702. At the top of the sample enclosure 702 is a brushless, DC motor 706 that powers an agitator (visible in FIGS. 9 and 10) used to agitate the drilling fluid. Located on top of the DC motor 706 is a motor cover 717. The DC motor 706 is secured to the sample enclosure 702 via a series of bolts 716 that secure the motor cover 717 to a flange 720 extending along the periphery of the top of the sample enclosure 702, thereby clamping the DC motor 706 to the sample enclosure 702. A handle 726 is bolted to the motor cover 717 to facilitate carrying of the gas trap 700. An explosion proof seal 730 is screwed into the motor cover 717 through which electrical connections (not shown) to the DC motor 706 can be made. A mounting tube 1000 (visible in FIG. 10) can be used to mount the gas trap 700 to the shaker box (not shown).

Adjacent to the sample enclosure 702 is the bubbler enclosure 704. At the bottom of the bubbler enclosure 704 is a bubbler air outlet 724, and at the top of the bubbler enclosure 704 is a bubbler enclosure cover 722. Extending from the top of the bubbler enclosure cover 722 is the tubing bundle 210 inside of which is the gas sample conduit 710, bubbler air conduit 712, and heat trace 714. The gas sample conduit 710 is fluidly coupled to the sample inlet 203 of the gas analyzer 114 and the bubbler air conduit 712 is fluidly coupled to the bubbler outlet 209 of the gas analyzer 114. During operation of the gas trap 700, the bubbler air conduit 712 is fluidly coupled to a bubbler air inlet in the form of a bubbler air port 918 that fluidly couples two sides of a bubbler enclosure baffle 922. Similarly, the sample air conduit 710 is fluidly coupled to a gas sample port 920 that fluidly couples the sample air conduit 710 to the interior of the sample enclosure 702.

Referring now to FIG. 9, the sample enclosure 702 is delineated by a sample enclosure wall that includes a sample enclosure wall portion 912 and a shared wall portion 914, while the bubbler enclosure 704 is desalinated by a bubbler enclosure wall that includes a bubbler enclosure wall portion 916 and the shared wall portion 914. In the depicted embodiment, the shared wall portion 914 delineates a portion of both the sample enclosure 702 and the bubbler enclosure 704; the sample enclosure wall portion 912 delineates the remainder of the sample enclosure 702 but not the bubbler enclosure 704; and the bubbler enclosure wall portion 916 delineates the remainder of the bubbler enclosure 704 but not the sample enclosure 702. Disposed along the shared wall portion 914 are two ports: a liquid port 908 that allows agitated drilling fluid to enter the bubbler enclosure 704 from the sample enclosure 702, and a gas port 910 that allows the bubbler air to enter the sample enclosure 702 from the bubbler enclosure 704. As discussed in more detail below, the presence of these two ports 908, 910 helps to keep the footprint of the gas trap 700 relatively small, while using bubbler air to maintain a constant drilling fluid level within the sample enclosure 702. Although in the present embodiment the sample enclosure 702 and the bubbler enclosure 704 are both cylindrical, in alternative embodiments they may be differently shaped. For example, the sample and bubbler enclosures 702, 704 may be polygonal (regular or irregular) in shape.

The agitator extends axially along the sample enclosure 702 and includes a shaft 900 that has disposed at one end a mixing portion 902. The mixing portion 902 is composed of a triangular mounting plate through the corners of which extend three bolts that help to displace and agitate the drilling fluid. The other end of the shaft 900 is inserted into a rotor 928 of the DC motor 706. The rotor 928 rotates relative to a stator 930, and both the rotor 928 and stator 930 rest on a shoulder 926 that is supported by the flange 720 on top of the sample enclosure 702. In the embodiment of FIG. 9, the DC motor 706 is frameless and the rotor 928 is directly coupled to the shaft 900 using an adhesive such as a retaining compound; in terms of reliability and integrity, directly coupling the shaft 900 to the rotor 928 is advantageous compared to using a typically designed, pre-assembled off-the-shelf motor in which the motor has an output shaft to which the shaft 900 is then coupled. One pair of bearings 932a is located above the rotor 928 and another pair of bearings 932b is located below the rotor 928. As the shaft 900 is threaded through the rotor 928, the surface of the shaft contacts the bearings 932a,b, which helps the shaft 900 to spin. Beneficially, because the DC motor 706 is frameless, the bearings 932a,b can be sized during assembly of the DC motor 706 in accordance with the length of the shaft 900, and the shaft 900 can be directly coupled to the rotor 928 as is done using the adhesive in the depicted exemplary embodiment. By assembling the DC motor 706 in this way, the bearings 932a,b can be selected to be sufficiently large such that they can withstand the forces applied to them by virtue of typical lateral or bending forces that are applied to the shaft 900 during its rotation. In order to keep the bearings 932a,b dry and operational, they are beneficially kept a relatively long distance from the drilling fluid, which dictates that the shaft 900 be relatively long relative to the spacing between the pairs of bearings 932a,b.

In the present example embodiment, the distance from the bottom pair of bearings 932b to the bottom of the mixing portion 902 of the shaft 900 (the "overhung load") is approximately 13.25 inches, while the spacing between the pairs of bearings 932a,b is approximately 2.5 inches. Since the distance ratio of the length of the overhung load to the spacing between the bearings 932a,b is over five, the bearings 932a,b are subject to moment loading that is relatively heavy and greater than a typically designed, pre-assembled off-the-shelf motor having the minimum power rating suitable for use in the depicted gas trap 700 is designed to withstand. One potential solution to this problem is to install an additional set of bearings along the interior surface of the sample enclosure 702 to reinforce the shaft 900; however, this is impractical given that splashing drilling fluid within the sample enclosure 702 would quickly clog these bearings. Another potential solution is to use an off-the-shelf, pre-assembled DC motor that has a higher power rating, and therefore larger bearings, than is required for the gas trap 700; however, this solution wastes power and is therefore relatively inefficient. Using a DC motor with a higher power rating also means that a motor that is heavier than necessary is used. By using the frameless, DC motor 706 and sizing the bearings 932a,b during assembly as opposed to using an off-the-shelf DC motor, a relatively efficient and practical solution to the problem of withstanding the forces that result from using the relatively long shaft 900 results. In the depicted example embodiment, each of each of the top pair of bearings 932a has dimensions of approximately 20 mm×42 mm×12 mm, and each of the bottom pair of bearings 932b has dimensions of approximately 25 mm×42 mm×9 mm. In the present example embodiment, the DC motor 706 can run at 250 watts (⅓ hp) maximum continuous power.

In the embodiment of FIG. 9, the shoulders 926 taper to form a passageway 934 that leads from the DC motor 706 to the sample enclosure 702. At the bottom of this passageway 934 is a sealing portion formed from a first sealing element in the form of a lip seal 936 and a second sealing element in the form of two seals 938a,b located between the lip seal 936 and the DC motor 706. A small gap is present between the shaft 900 and the sealing portion to act as a flame path so as to prevent combustible gases outside of the DC motor 706 from igniting in the event that an explosion occurs within the DC motor 706. In the present embodiment, the gas trap 700 is machined such that the width of the gap is between 0.002 of an inch and 0.006 of an inch; in alternative embodiments, the width of the gap may differ. The sealing portion fits closely around the shaft 900 so as to prevent agitated drilling fluid from splashing up into the DC motor 706. Specifically, the lip seal 936 is particularly designed to prevent solid particulates from entering the DC motor 706, while the two seals 938a,b are designed to prevent liquid from entering the DC motor 706. In the present embodiment the lip seal 936 is made from Buna-N rubber and the two seals 938a,b are made from graphite filled PTFE (Teflon), but in alternative embodiments the seals 936, 938a,b may be made from different materials. At a point of relatively high loading immediately below the bottom pair of bearings 932b, the shaft 900 has a diameter of approximately 0.975 inches; at a point of relatively low loading just below the flame path, the shaft 900 has a diameter of approximately 0.7 inches.

A baffle 924 located below the shoulders 926 with an opening to allow the shaft 900 to pass through also helps to prevent splashing drilling fluid from plugging the gas sample port 920.

A polyurethane disc 940 placed on the shaft 900 and aligned with, and located slightly below, the opening in the baffle 924 also helps to prevent splashing drilling fluid from entering the inside of the DC motor 706.

The gas trap 700 is configured to be able to use the bubbler air to maintain a certain height of the drilling fluid when the drilling fluid is greater than the marker labelled L1 in FIG. 9. L1 corresponds to the location of the bubbler air outlet 724. During normal operation, the pressures of the sample enclosure 702 and the bubbler enclosure 704 are equalized by virtue of air being able to pass freely through the gas port 910. Consequently, when the bubbler air is sufficiently pressurized, the bubbler air forces the drilling fluid in both the sample and bubbler enclosures 702, 704 down to L1 prior to exiting the bubbler enclosure 704 through the bubbler air outlet 724. In the present exemplary embodiment, the bubbler air is pressurized to approximately 0.5 psi; in alternative embodiments the bubbler air may be pressurized to a different level depending on, for example, the density of the drilling fluid and the dimensions of the gas trap 700.

When no bubbler air is being injected into the gas trap 700, the gas trap 700 is beneficially immersed no deeper than the marker labelled L2 in FIG. 9, which corresponds to the location of the gas port 910. This is because the when there is no bubbler air, the drilling fluid will rise to level L2. Keeping the drilling fluid lower than L2 reduces the likelihood that the drilling fluid will plug any or all of the gas port 910, the bubbler air port 918, and the gas sample port 920 which could prejudice operation of the gas trap 700.

In order to liberate gases that are entrained in the drilling fluid, the DC motor 706 rotates the agitator, which consequently agitates the drilling fluid. Agitation of the drilling fluid consequently results in the gas sample being released into the sample enclosure 702. The sample pump 214 in the gas analyzer 114 sucks the sample gas from the sample enclosure 702, through the gas sample port 920 and the gas sample conduit 710, and into the gas analyzer 114 via the sample inlet 203 for analysis as described above. While the drilling fluid is being agitated, the bubbler pump 232 outputs pressurized bubbler air out through the bubbler outlet 209, the bubbler air conduit 712, the bubbler air port 918, and into the sample enclosure 702 and the bubbler enclosure 704 so as to maintain the level of drilling fluid within the sample enclosure 702 substantially constant at level L1. Beneficially, as the bubbler pump 232 is dedicated to providing the bubbler air, problems associated with pressure variations in rig air are avoided. Furthermore, as the heat trace 714 can be operated to prevent the bubbler air from freezing, contaminants such as alcohol and antifreeze do not need to be added to the bubbler air. Additionally, because of the heat trace 714, moisture does not need to be removed from the gas sample using a desiccant to prevent freezing as may be done in conventional systems.

After the gas sample is liberated from the drilling fluid, the agitated drilling fluid exits the sample enclosure 702 and enters the bubbler enclosure 704 via the liquid port 908. Because the drilling fluid directly enters the bubbler enclosure 704 from the sample enclosure 702, no external baffles or containers need to be placed outside of the sample or bubbler enclosures 702, 704 to prevent splashing or to otherwise direct the drilling fluid after it leaves the gas trap 700. Instead, the drilling fluid exits the gas trap 700 by being forced out through the bubbler air outlet 724 at the bottom of the bubbler enclosure 704, which substantially mitigates any problems related to splashing.

In the present embodiment the liquid port 908 is used primarily to allow the agitated drilling fluid to exit the sample enclosure 702 and to enter the bubbler enclosure 704, and the gas port 910 is used primarily to allow gases to be exchanged between the sample and bubbler enclosures 702, 704 so as to equalize pressure between the two enclosures 702, 704. However, gases may pass through the liquid port 908 and the liquid port 908 may therefore also contribute to equalizing pressures between the enclosures 702, 704. Similarly, depending on the height of the drilling fluid, some of the agitated drilling fluid may enter the bubbler enclosure 704 from the sample enclosure 702 via the gas port 910. In alternative embodiments (not depicted), a single fluid port may be used to both allow drilling fluid to enter the bubbler enclosure 704 from the sample enclosure 702 and to equalize pressure between the two enclosures 702, 704; multiple fluid ports may be used to both allow drilling fluid to enter the bubbler enclosure 704 from the sample enclosure 702 and to equalize pressure between the two enclosures 702, 704; or a combination of any of fluid ports that operate to both allow drilling fluid to enter the bubbler enclosure 704 from the sample enclosure 702 and to equalize pressure between the two enclosures 702, 704, liquid ports 908 that operate primarily to allow the agitated drilling fluid to exit the sample enclosure 702 and to enter the bubbler enclosure 704, and gas ports 910 that operate primarily to allow gases to be exchanged between the sample and bubbler enclosures 702, 704 so as to equalize pressure between the two enclosures 702, 704 may be used.

Beneficially over an AC induction motor, the DC motor 706 generates significantly less waste heat (the DC motor 706 can be 80-85% efficient, while an AC induction motor is typically around 50% efficient) and is operable at a user-controllable rate independent of the frequency of the AC electricity used to power the motor. Additionally, the controller (not shown) used with the DC motor 706 is able to inherently measure the operating speed and the torque generated by the DC motor 706, which are respectively directly proportional to the degree to which the drilling fluid is being agitated and how much work the DC motor 706 is performing. With an AC induction motor, such measurements are typically obtained not through any kind of motor controller, but through a more complex arrangement of sensors mounted to or near the motor, or such measurements are not used at all and the AC induction motor is run in an open loop configuration. Furthermore, beneficially compared to an air motor, the DC motor 706 is operable independently of the current air pressure available through the rig air and is not contaminated by any contaminants present in the rig air. The DC motor 706 is also significantly lighter than a typical AC induction motor; the DC motor 706 can weigh approximately three to four pounds, while a typical AC induction motor can weigh roughly an order of magnitude more, or about 30 pounds.

In the depicted embodiment, the gas trap 700 is shown as using the DC motor 706 to power agitation and the liquid port 908 to discharge agitated drilling fluid from the sample enclosure 902 to the bubbler enclosure 904. However, in alternative embodiments (not shown) the gas trap 700 may use the DC motor 706 without discharging agitated drilling fluid into the bubbler enclosure 904, or the gas trap 700 may discharge agitated drilling fluid into the bubbler enclosure 904 via the liquid port 908 without incorporating the DC motor 706. For example, according to one alternative embodiment (not shown), the gas trap shown in U.S. Pat. No. 6,666,099 may be modified to be powered using the DC motor 706.

Furthermore, in the depicted embodiment, the gas trap may be made from a material such as stainless steel. In alternative embodiments, any suitable material can be used, such as a corrosion resistant alloy or a material that is not corrosion resistant so long as appropriate corrosion allowances are considered. Furthermore, in the depicted embodiment the sample enclosure 702 and the bubbler enclosure 704 share the shared wall portion 914. In an alternative embodiment (not depicted), there does not need to be any shared wall portion between the sample and bubbler enclosures 702, 704. For example, the sample and bubbler enclosures 702, 704 may both be cylindrical in shape and separate from each other, but there may be a fluid conduit such as tubing that fluidly couples the sample and bubbler enclosures 702, 704 together. The fluid conduit may optionally be slanted downwards from the sample enclosure 702 towards the bubbler enclosure 704 so as to facilitate emptying of drilling fluid into the bubbler enclosure 704.

Any of the foregoing methods may be encoded on a computer readable medium for execution by a processor such as the microprocessor 302, the DSP 300, a programmable logic controller, a field programmable gate array, a controller, and an application specific integrated circuit. The computer readable medium may be, for example, the SDRAM 322, the calibration flash RAM 324, the firmware flash RAM 326, disc-based media such as DVD-ROMs, read only memories such as EEPROMs, any suitable magnetic storage media such as hard drives, and any other suitable type of storage medium.

For the sake of convenience, the embodiments above are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or features of the flexible interface can be implemented by themselves, or in combination with other operations in either hardware or software.

While particular embodiments have been described in the foregoing, it is to be understood that other embodiments are possible and are intended to be included herein. It will be clear to any person skilled in the art that modifications of and adjustments to the foregoing embodiments, not shown, are possible.

The invention claimed is:

1. An apparatus for liberating gases from drilling fluid, the apparatus comprising:
   a sample enclosure having a liquid inlet and a gas sample outlet;
   an agitator disposed within the sample enclosure and configured to agitate drilling fluid located within the sample enclosure to liberate gases entrained in the drilling fluid so that the gases can exit through the gas sample outlet;
   a brushless, DC motor rotatably coupled to the agitator to power the agitator;
   a motor cover covering at least a portion of the brushless, DC motor and an explosion proof seal secured to the motor cover, the explosion proof seal permitting electrical connections to be made to the DC motor;
   wherein the agitator comprises a shaft having a mixing portion shaped to facilitate agitation of the drilling fluid, and wherein the brushless DC motor comprises a stator and a rotor directly coupled to the shaft and rotatable relative to the stator in order to rotate the shaft;
   further comprising a sealing portion disposed around the shaft and between the DC motor and the sample enclosure, the sealing portion comprising a first sealing element configured to prevent solid particulates from entering the brushless DC motor and a second sealing element configured to prevent liquid from entering the brushless DC motor, wherein the first sealing element is nearer to the sample enclosure than the second sealing element,
   further comprising a flame path comprising a gap between the shaft and the sealing portion, the flame path acting to prevent combustible gases outside of the DC motor from igniting in the event that an explosion occurs within the DC motor.

2. An apparatus as claimed in claim 1 further comprising a bubbler enclosure having a bubbler air inlet and a bubbler air outlet, and fluidly coupled to the sample enclosure such that the sample and bubbler enclosures are equally pressurized so that sufficiently pressurized bubbler air entering through the bubbler air inlet maintains the drilling fluid in the sample enclosure at a level determined by the location of the bubbler air outlet when the liquid inlet and the bubbler air outlet are both submerged in the drilling fluid, and such that agitated drilling fluid enters the bubbler enclosure from the sample enclosure.

3. An apparatus as claimed in claim 2 further comprising:
   a bubbler air conduit fluidly coupled to the bubbler air inlet to transport the pressurized bubbler air from outside of the apparatus to the bubbler enclosure; and
   a heat trace thermally coupled to the bubbler air conduit.

4. An apparatus as claimed in claim 2 further comprising:
   a gas sample conduit fluidly coupled to the gas sample outlet to transport the gas sample away from the sample enclosure;
   a bubbler air conduit fluidly coupled to the bubbler air inlet to transport the pressurized bubbler air from outside of the apparatus to the bubbler enclosure; and
   a heat trace thermally coupled to both the gas sample and bubbler air conduits.

5. An apparatus as claimed in claim 2 further comprising a gas analyzer comprising a bubbler pump fluidly coupled to an air source and configured to output the pressurized bubbler air, wherein the bubbler air inlet is fluidly coupled to the bubbler pump to receive the pressurized bubbler air.

6. An apparatus as claimed in claim 1 wherein the second sealing element comprises two seals.

7. An apparatus as claimed in claim 1 further comprising a disc disposed along the shaft to prevent the drilling fluid from entering the DC motor.

8. An apparatus as claimed in claim 1 further comprising:
   a gas sample conduit fluidly coupled to the gas sample outlet to transport the gas sample away from the sample enclosure; and
   a heat trace thermally coupled to the gas sample conduit.

9. An apparatus as claimed in claim 1 wherein the shaft is directly coupled to the rotor using an adhesive.

10. An apparatus as claimed in claim 1 wherein the DC motor is frameless.

11. An apparatus as claimed in claim 10 further comprising bearings located above and below the rotor, the bearings contacting the shaft to facilitate rotation of the shaft.

12. A method for liberating gases entrained in a drilling fluid, the method comprising:
submerging a liquid inlet of a sample enclosure in the drilling fluid; and
agitating the drilling fluid within the sample enclosure to liberate the gases entrained therein by using a brushless DC motor,
wherein a motor cover covers at least a portion of the brushless DC motor and an explosion proof seal is secured to the motor cover, the explosion proof seal permitting electrical connections to be made to the brushless DC motor;
wherein the brushless DC motor comprises a stator and a rotor directly coupled to a shaft extending from the brushless DC motor and rotatable relative to the stator in order to rotate the shaft, wherein rotation of the shaft results in the agitation;
sealing the DC motor using a sealing portion disposed around the shaft and between the DC motor and the sample enclosure, the sealing portion comprising a first sealing element configured to prevent solid particulates from entering the DC motor and a second sealing element configured to prevent liquid from entering the DC motor, wherein the first sealing element is nearer to the sample enclosure than the second sealing element,
wherein a flame path comprising a gap is present between the shaft and the sealing portion, the flame path acting to prevent combustible gases outside of the DC motor from igniting in the event that an explosion occurs within the DC motor.

13. A method as claimed in claim 12 further comprising:
submerging a bubbler air outlet of a bubbler enclosure in the drilling fluid, wherein the sample and bubbler enclosures are fluidly coupled together such that they are equally pressurized and such that the drilling fluid agitated in the sample enclosure enters the bubbler enclosure; and
pressurizing the sample and bubbler enclosures using pressurized bubbler air such that the drilling fluid in the sample enclosure is at a level determined by the location of the bubbler air outlet.

14. A method as claimed in claim 13 further comprising conveying the bubbler air to the bubbler enclosure using a heated bubbler air conduit.

15. A method as claimed in claim 13 further comprising conveying the gases liberated from the drilling fluid away from the sample enclosure using a gas sample conduit and conveying the bubbler air to the bubbler enclosure using a bubbler air conduit, and wherein the gas sample and bubbler air conduits are both heated.

16. A method as claimed in claim 13 further comprising generating the bubbler air by using a pump located within a gas analyzer.

17. A method as claimed in claim 12 further comprising blocking splashing drilling fluid from entering the DC motor with a disc disposed along the shaft.

18. A method as claimed in claim 12 further comprising conveying the gases liberated from the drilling fluid away from the sample enclosure using a heated gas sample conduit.

19. A method as claimed in claim 12 wherein the shaft is directly coupled to the rotor using an adhesive.

20. A method as claimed in claim 12 wherein the DC motor is frameless.

21. A method as claimed in 20 wherein bearings are located above and below the rotor, the bearings contacting the shaft to facilitate rotation of the shaft.

* * * * *